US011333625B2

(12) United States Patent
Jones et al.

(10) Patent No.: US 11,333,625 B2
(45) Date of Patent: May 17, 2022

(54) ELECTROCHEMICAL HYDROGEN SENSOR

(71) Applicant: Schlumberger Technology Corporation, Sugar Land, TX (US)

(72) Inventors: Timothy Jones, Cambridge (GB); Debbie S. Silvester, Perth (AU); Li Jiang, Katy, TX (US); Hanpu Liang, Cambridge (GB); Nathan Lawrence, Huntingdon (GB); Richard Compton, Oxford (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 16/871,735

(22) Filed: May 11, 2020

(65) Prior Publication Data

US 2020/0271617 A1    Aug. 27, 2020

Related U.S. Application Data

(63) Continuation of application No. 14/436,221, filed as application No. PCT/IB2013/059370 on Oct. 15, 2013, now Pat. No. 10,962,499.

(30) Foreign Application Priority Data

Oct. 16, 2012   (GB) ..................... 1218514

(51) Int. Cl.
*G01N 27/404*   (2006.01)
*B01J 19/24*   (2006.01)
(Continued)

(52) U.S. Cl.
CPC .......... *G01N 27/4045* (2013.01); *B01J 19/24* (2013.01); *E21B 49/08* (2013.01);
(Continued)

(58) Field of Classification Search
CPC .... G01N 27/4045; G01N 27/30; G01N 27/40; G01N 27/4162; G01N 27/49;
(Continued)

(56) References Cited

U.S. PATENT DOCUMENTS 3,468,781 A * 9/1969 Lucero ............... G01N 27/4045
                                                204/415
3,509,034 A    4/1970 Paine
(Continued)

FOREIGN PATENT DOCUMENTS

EP    1227141 A2    7/2002
EP    1921445 A1    5/2008
(Continued)

OTHER PUBLICATIONS

Silvester et al. (DS Silvester, L Aldous, C Hardacre, RG Compton, An electrochemical study of the oxidation of hydrogen at platinum electrodes in several room temperature ionic liquids, J. Phys. Chem. B 111 (2007) 5000-5007) (Year: 2007).*
(Continued)

*Primary Examiner* — Joshua L Allen

(57) ABSTRACT

A process for determining a content of hydrogen in a fluid medium includes contacting the fluid medium with a sensor. The sensor has a housing enclosing a chamber containing an ionic liquid electrolyte, a window which is permeable to hydrogen and positioned in an opening in the housing, and electrodes in contact with the ionic liquid electrolyte in the chamber. Hydrogen is allowed to pass through the window from the fluid medium into the electrolyte and the sensor is heated. Temperature and pressure of the fluid medium is determined and electrical potential is applied to the electrodes. The method also includes measuring current flow. The sensor can be used to observe hydrogen concentration by voltammetry. The method and sensor may be used for measuring downhole hydrogen content, monitoring fiber-
(Continued)

optic cables for damage by hydrogen, corrosion monitoring, and in small-scale process plants where hydrogen is part of a gas stream.

20 Claims, 8 Drawing Sheets

(51) Int. Cl.
| | |
|---|---|
| *E21B 49/08* | (2006.01) |
| *G01N 27/30* | (2006.01) |
| *G01N 27/40* | (2006.01) |
| *G01N 27/416* | (2006.01) |
| *G01N 27/49* | (2006.01) |
| *H01M 8/0438* | (2016.01) |
| *H01M 8/1018* | (2016.01) |
| *G01N 33/00* | (2006.01) |
| *H01M 8/10* | (2016.01) |

(52) U.S. Cl.
CPC ............. *G01N 27/30* (2013.01); *G01N 27/40* (2013.01); *G01N 27/4162* (2013.01); *G01N 27/49* (2013.01); *H01M 8/04388* (2013.01); *H01M 8/1018* (2013.01); *B01J 2219/24* (2013.01); *G01N 33/005* (2013.01); *H01M 2008/1095* (2013.01)

(58) Field of Classification Search
CPC .............. G01N 33/005; G01N 27/413; G01N 27/406–41; G01N 33/0004–0075; B01J 19/24; B01J 2219/24; E21B 49/08; H01M 8/04388; H01M 8/1018; H01M 2008/1095; Y02E 60/50
See application file for complete search history.

(56) References Cited

U.S. PATENT DOCUMENTS

| | | | |
|---|---|---|---|
| 4,221,651 A | 9/1980 | Mansfeld et al. | |
| 4,241,790 A | 12/1980 | Magnie | |
| 4,293,399 A * | 10/1981 | Belanger ............ | G01N 27/4045 204/415 |
| 4,563,249 A * | 1/1986 | Hale ................... | G01N 27/4045 204/415 |
| 4,857,080 A * | 8/1989 | Baker ................. | B01D 67/0072 95/56 |
| 4,879,005 A | 11/1989 | Fray et al. | |
| 4,882,031 A * | 11/1989 | Furuya ............... | G01N 27/4162 204/415 |
| 5,041,204 A | 8/1991 | Haupt et al. | |
| 5,279,795 A | 1/1994 | Hughes et al. | |
| 5,316,648 A | 5/1994 | Kuhn et al. | |
| 5,829,520 A * | 11/1998 | Johnson .................. | E21B 47/01 166/250.01 |
| 5,858,204 A | 1/1999 | Jambo et al. | |
| 6,016,867 A | 1/2000 | Gregoli et al. | |
| 6,037,592 A | 3/2000 | Sunshine et al. | |
| 6,214,195 B1 | 4/2001 | Yadav et al. | |
| 6,324,891 B1 * | 12/2001 | Gibeault ............ | G01N 33/2841 73/19.01 |
| 6,519,041 B1 | 2/2003 | Berthold | |
| 6,550,304 B2 | 4/2003 | Lloyd et al. | |
| 6,634,213 B1 | 10/2003 | Oconnor et al. | |
| 6,841,292 B2 | 1/2005 | Nelson et al. | |
| 6,866,950 B2 | 3/2005 | Connor et al. | |
| 6,867,364 B2 | 3/2005 | Hafskjold et al. | |
| 6,887,606 B2 | 5/2005 | Parr et al. | |
| 6,913,847 B2 | 7/2005 | Wells et al. | |
| 6,939,717 B2 | 9/2005 | Jiang et al. | |
| 6,995,360 B2 | 2/2006 | Jones et al. | |
| 7,060,169 B2 | 6/2006 | Rohrl | |
| 7,087,334 B2 | 8/2006 | Sugino et al. | |
| 7,169,490 B2 | 1/2007 | Barton et al. | |
| 7,189,364 B2 | 3/2007 | Nadanami et al. | |
| 7,258,773 B2 | 8/2007 | Zhou et al. | |
| 7,368,192 B2 | 5/2008 | Pettit et al. | |
| 7,442,455 B2 | 10/2008 | Kojima et al. | |
| 7,841,228 B2 | 11/2010 | Farnsworth | |
| 10,962,499 B2 | 3/2021 | Silvester et al. | |
| 2003/0077495 A1 | 4/2003 | Scartozzi et al. | |
| 2003/0225169 A1 | 12/2003 | Yetman | |
| 2004/0050143 A1 * | 3/2004 | Hoagland .............. | G01N 31/10 73/31.05 |
| 2004/0238353 A1 | 12/2004 | Kato et al. | |
| 2004/0261500 A1 * | 12/2004 | Ng ......................... | B82Y 15/00 73/31.05 |
| 2005/0045493 A1 * | 3/2005 | Mahurin ............ | G01N 33/0047 205/775 |
| 2005/0106086 A1 | 5/2005 | Tomlinson et al. | |
| 2005/0189223 A1 * | 9/2005 | Yamaguchi .......... | G01N 27/125 204/431 |
| 2006/0234113 A1 | 10/2006 | Rohrl | |
| 2006/0249382 A1 | 11/2006 | Hengstenberg et al. | |
| 2006/0278536 A1 | 12/2006 | Burrell et al. | |
| 2007/0068222 A1 | 3/2007 | Zeng et al. | |
| 2007/0108052 A1 * | 5/2007 | Luongo ................ | G01N 33/005 204/431 |
| 2008/0090126 A1 | 4/2008 | Unoki et al. | |
| 2008/0153174 A1 * | 6/2008 | Galloway ............ | G01N 33/005 436/144 |
| 2008/0241022 A1 | 10/2008 | Nariai et al. | |
| 2008/0262110 A1 | 10/2008 | Lomax et al. | |
| 2009/0238753 A1 | 9/2009 | Galloway et al. | |
| 2009/0277625 A1 | 11/2009 | Bai et al. | |
| 2009/0299795 A1 | 12/2009 | Khan et al. | |
| 2009/0312964 A1 * | 12/2009 | Najim Al-Khamis ....................... | E21B 43/34 702/50 |
| 2010/0000153 A1 | 1/2010 | Kurkjian et al. | |
| 2010/0008632 A1 * | 1/2010 | Herbst ................. | G02B 6/4415 385/109 |
| 2010/0025110 A1 * | 2/2010 | John ....................... | E21B 44/00 175/27 |
| 2010/0089456 A1 * | 4/2010 | Lowery ................ | G05D 7/0106 137/1 |
| 2010/0212893 A1 * | 8/2010 | Araghi .................... | E21B 43/24 166/272.1 |
| 2011/0174052 A1 | 7/2011 | Kuebel | |
| 2015/0247818 A1 | 9/2015 | Silvester et al. | |

FOREIGN PATENT DOCUMENTS

| | | | | |
|---|---|---|---|---|
| GB | 239765 A | | 9/1925 | |
| GB | 2395564 B | | 12/2004 | |
| GB | 2399651 B | | 8/2005 | |
| GB | 2417561 A | | 3/2006 | |
| GB | 2426343 B | | 9/2007 | |
| GB | 2476057 A | * | 6/2011 | ......... G01N 27/3335 |
| JP | 06223850 A | * | 8/1994 | |
| JP | 2012163506 A | | 8/2012 | |
| WO | 2008110830 A1 | | 9/2008 | |
| WO | 2009126568 A1 | | 10/2009 | |
| WO | 2010063624 A1 | | 6/2010 | |

OTHER PUBLICATIONS

Hashizaki (JPH06223850 A, machine translation). (Year: 1993).*
Jin et al. (X Jin, L Yu, D Garcia, RX Ren, X Zeng, Ionic liquid high-temperature gas sensor array, Anal. Chem. 78 (2006) 6980-6989) (Year: 2006).*
Search Report and Written Opinion of International Patent Application No. PCT/IB2013/059370, dated Jul. 18, 2014, 13 pages.
Preliminary Report on Patentability of International Patent Application No. PCT/IB2013/059370, dated Apr. 30, 2015, 9 pages.
Silvester, et al., "An Electronchemical Study of the Oxidation of Hydrogen at Platinum Electrodes in Several Room Temperature Ionic Liquids," J. Phys. Chem. B. 2007, 111, American Chemical Society, pp. 5000-5007.

(56) References Cited

OTHER PUBLICATIONS

Ockwig and Nenoff, "Additions and Corrections Membranes for Hydrogen Separation," Chemical Reviews, 2010, vol. 110, No. 4, pp. 2573-2574.

Modak, "Haber Process for Ammonia Synthesis," Resonance, 2011, 7, pp. 69-77.

Examination Report of UK Patent Application No. 1218514.6 dated Oct. 11, 2017, 3 pages.

Yu et al., "Research Surveys of Electrochemical Sensors for in-situ Determining Hydrogen in Steels," J. Mater. Sci. Technol., vol. 16 No. 3, 2000, pp. 305-310.

Barbir, "PEM Fuel Cells: Theory and Practice", Elsevier Academic Press, Amsterdam, 2005, pp. 411-416.

Silvester, D. et al., "Reference Electrodes for use in RTI Ls.", Chapter 13.2 in Electrodeposition in Ionic liquids, Endres, F., MacFarlane, D., Abbot, A., Eds., Wiley, New York, 2008.

Mansfeld et al., "Barnacle Electrode Measurement System for Hydrogen in Steels," National Association of Corrosion Engineers, Feb. 1982, pp. 35-38.

Bartholomew and Farrauto "Fundamentals of Industrial Catalytic Processes", 2nd Edition, pp. 412-415, Wiley-Interscience, 2006, pp. 382-398.

Cai et al., Journal of East China Normal University (Natural Science), No. 3, 2001, 4 pages.

Jin et al., Ionic liquid high-temperature gas sensor array, Anal. Chem. 78, 2006, pp. 6980-6989.

Lee, R. W. et al., "Diffusion of Hydrogen and Deuterium in Fused Quartz", Journal of Chemical Physics, 1962, 36(4), pp. 1062-1071.

Lemaire, P.J., "Reliability of Optical Fibers Exposed to Hydrogen: Prediction of Long-Term Loss Increases", Optical Engineering, 1991, 30(6), pp. 780-789.

Liang, H-P. et al., "Controllable Synthesis of Hollow Hierarchical Palladium Nanostructures with Enhanced Activity for Proton/Hydrogen Sensing", Journal of Physical Chemistry C, 2008,112(2), pp. 338-344.

Lin, H. H. et al., "A Porous Silicon-Palladium Composite Film for Optical Interferometric Sensing of Hydrogen", Langmuir, 2004, 20(12), pp. 5104-5108.

Lu, X. et al., "Solid-state Amperometric Hydrogen Sensor Based on Polymer Electrolyte Membrane Fuel Cell", Sensors and Actuators B: Chemical, 2005, 107(2), pp. 812-817.

Mayer, W. et al., "Propellant Injection in a Liquid Oxygen/Gaseous Hydrogen Rocket Engine", Journal of Propulsion and Power, 1996, 12(6), pp. 1137-1147.

Mishra, V. N. et al., "Thick-Film Hydrogen Sensor", Sensors and Actuators B: Chemical, 1998, 21(3), pp. 209-212.

Modak, J. M., "Haber Process for Ammonia Synthesis", Resonance, 2011, 7(9), pp. 1159-1167.

Morris, D. R. et al., "Electrochemical Sensors for Monitoring Hydrogen in Steel", Corrosion Engineering, 1994, 50 (8), pp. 641-647.

Morris, D. R., et al., "A Solid-State Potentiometric Sensor for Monitoring Hydrogen in Commercial Pipeline Steel", Corrosion Engineering, 1995, 51(4), pp. 301-311.

Ockwig, N.W. et al., Membranes for Hydrogen Separation, Chemical Review, 2007, 107(10), pp. 4078-4110.

O'Hayre, R. et al., "Fuel Cell Fundamentals", John Wiley and Sons, New York, 2006, pp. 258-265.

O'Mahony, A. M. et al, "The Electrochemical Reduction of Hydrogen Sulfide on Platinum in Several Room Temperature Ionic Liquids", Journal of Physical Chemistry C, 2008, 112(20), pp. 7725-7730.

O'Mahony, A. M. et al., "Effect of Water on the Electrochemical Window and Potential Limits of Room-Temperature Ionic Liquids", Journal of Chemistry Engineering Data, 2008, 53(12), pp. 2884-2891.

Paglieri, S. N. et al., "Innovations in Palladium Membrane Research", Separation and Purification Methods 2002, 31(1), pp. 1-169.

Patel, S. V. et al., "Film Structure and Conductometric Hydrogen-Gas-Sensing Characteristics of Ultrathin Platinum Films", Langmuir, 1999, 15(9), pp. 3307-3311.

Plotnichenko, V. G. et al., "Influence of Molecular Hydrogen Diffusion on Concentalion and Distribution of Hydroxyl Groups in Silica Fibers", Journal of Lightwave Technology, 2005, 23(1), pp. 341-347.

Qian, D.-J. et al., "A Hydrogen Biosensor Made of Clay, Poly(Butylviologen), and Hydrogenase Sandwiched on a Glass Carbon Electrode", Biosensors and Bioelectronics, 2002, 17, pp. 789-796.

Ramos, R. T. et al., "Survivability of Optical Fiber for Harsh Environments", Society of Petroleum Engineers, Presented at the Annual Technical Conference and Exhibition, 2008, SPE 116075, 2008, pp. 1-10.

Rogers, E. I. et al., "Voltammetric Characterization of the Ferrocene|Ferrocenium and Cobaltocenium|Cobaltocene Redox Couples in RTILs", Journal of Physical Chemistry C, 2008, 112(7), pp. 2729-2735.

Sakthivel, M. et al., "Development of a Hydrogen Sensor Based on Solid Polymer Electrolyte Membranes", Sensors and Actuators B: Chemical, 2006, 113, pp. 998-1004.

Sakthivel, M., et al., "A Portable Limiting Current Solid-state Electrochemical Diffusion Hole Type Hydrogen Sensor Device for Biomass Fuel Reactors: Engineering Aspect", International Journal of Hydrogen Energy, 2008, 33(2), pp. 905-911.

San Marchi, C. et al., "Permeability, Solubility and Diffusivity of Hydrogen Isotopes in Stainless Steels at High Gas Pressures", International Journal of Hydrogen Energy, 2007, 32(1), pp. 100-116.

Scharnagl, K. et al., "Hydrogen Detection at High Concentalions with Stabilised Palladium", Sensors and Actuators B: Chemical, 2001, 78(1-3), pp. 138-143.

Schroder, U. et al., "Water-induced accelerated ion diffusion: voltammetric studies in 1-methyl-3-[2,6-(S)-dimethylocten-2-yl]imidazolium tetrafluoroborate, 1-butyl-3-methylimidazolium tetrafluoroborate and hexafluorophosphate ionic liquids", New Journal Chemistry 2000, 24, pp. 1009-1015.

Seeberger, A. et al., "Prediction of Long-Term Stability of Ionic Liquids at Elevated Temperatures", Physical Chemistry Chemical Physics, 2009, 11(41), pp. 9375-9381.

Silvester, D. S. et al., "The Electrochemical Oxidation of Hydrogen at Activated Platinum Electrodes in Room Temperature Ionic Liquids as Solvents", Journal of Electroanalytical Chemistry, 2008, 618(1-2), pp. 53-60.

Silvester, D. S. et al., "Electrochemistry in Room Temperature Ionic Liquids: A Review and Some Possible Applications", Z. Phys. Chem. 2006, 220, pp. 1247-1274.

Slaman, M. et al., "Fiber Optic Hydrogen Detectors Containing Mg-Based Metal Hydrides", Sensors and Actuators B: Chemical, 2007, 123(1), pp. 538-545.

"Standard Test Method for Electrochemical Measurement of Diffusible Hydrogen in Steels (Barnacle Electrode)", ASTM Designation: F 1113-87, Reapproved 2005, 6 pages.

Stone, J., "Interactions of Hydrogen and Deuterium with Silica Optical Fibers: A Review", Journal of Lightwave Technology, 1987, 5(5), pp. 712-733.

Swatloski, R. P. et al., "Ionic Liquids Are Not Always Green: Hydrolysis of 1-butyl-3-methylimidazolium hexafluorophosphate", Green Chemistry, 2003, 5(4), pp. 361-363.

Tabib-Azar, M. et al., "Highly Sensitive Hydrogen Sensors Using Palladium Coated Fiber Optics with Exposed Cores and Evanescent Field Interactions", Sensors and Actuators B: Chemical, 1999, 56(1-2), pp. 158-163.

Tomita, A. et al., "Hydrogen-Induced Loss Increases in Germanium-Doped Single-Mode Optical Fibres: Long-Term Predictions", Electronics Letters, 1985, 21(2), pp. 71-72.

Trouillet, A. et al., "Fibre Gratings for Hydrogen Sensing", Measurement Science and Technology, 2006, 17, pp. 1124-1128.

Tsuji, K. et al., "Simultaneous Determination of Hydrogen, Methane and Carbon Dioxide of Breath Using Gas-Solid Chromatography", Journal of Nutritional Science and Vitaminology, 1992, 38, pp. 103-109.

(56) References Cited

OTHER PUBLICATIONS

Urukova, I. et al., "Solubility of CO2, CO, and H2 in the Ionic Liquid [bmim][PF6] from Monte Carlo Simulations", Physical Chemistry B, 2005, 109(24), pp. 12154-12159.
Varfolomeev, S. D., et al., "Direct Electron Transfer Effect Biosensors", Biosensors and Bioelectronics, 1996, 11(9), pp. 863-871.
Walter, E. C. et al., "Palladium Mesowire Arrays for Fast Hydrogen Sensors and Hydrogen-Actuated Switches", Analytical Chemistry, 2002, 74(7), pp. 1546-1553.
Wang, R. et al., "A Novel Amperometric O2 Gas Sensor Based on Supported Room-Temperature Ionic Liquid Porous Polyethylene Membrane-Coated Electrodes", Electroanalysis, 2004, 16(1-2), pp. 66-72.
Wei, X. et al., "Nano-structured Pd-long Period Fiber Gratings Integrated Optical Sensor for Hydrogen Detection", Sensors and Actuators B: Chemical, 2008, 134, pp. 687-693.
Wu, J. et al., "A review of PEM Fuel Cell Durability: Degradation Mechanisms and Mitigation Strategies", Journal of Power Sources, 2008, 184(1), pp. 104-119.
Xue, H. et al, "Review of Ionic Liquids with Fluorine-Containing Anions", Journal of Fluorine Chemistry, 2006, 127(2), pp. 159-176.
Yu, G. et al., "Research Surveys of Electrochemical Sensors for In-Situ Determing Hydrogen in Steels", Journal of Materials Science Technology, 2000, 16(3), pp. 305-310.
Yu, L. et al., Ionic Liquid High Temperature Gas Sensors, Chemical Communications, 2005, pp. 2277-2279.
Zambov, L. et al., "Advanced Chemical Vapor Deposition Silicon Carbide Barrier Technology for Ultralow Permeability Applications", Journal of Vacuum Science and Technology. A, 2006, 24(5), pp. 1706-1713.
Zhao, Z. et al., "Humidity Effects on Pd/Au-based All-optical Hydrogen Sensors", Sensors and Actuators B: Chemical, 2008, 129(2), pp. 726-733.
Exam Report of UK Patent Application No. 1218514.6 dated May 3, 2017, 6 pages.
Search Report of UK Patent Application No. 1218514.6 dated Jan. 4, 2013, 4 pages.
Office Action and Search Report issued in Norwegian Patent Application No. 20150535, dated Oct. 6, 2020, 5 pages.
Addach, H. et al., "Quantitative Determination of Hydrogen in Solids by Gas Chromatography", Journal of Chromatography A, 2004, 1057, pp. 219-223.
Anthony, J. L. et al., "Solubilities and Thermodynamic Properties of Gases in the Ionic Liquid 1-n-Butyl-3-methylimidazolium Hexafluorophosphate", Journal of Physical Chemistry B, 2002, 106(29), pp. 7315-7320.
Athayde, A.L., "Metal Composite Membranes for Hydrogen Separation", Journal of Membrane Science, 1994, 94(1), pp. 299-311.
Barbir, F., "PEM Fuel Cells: Theory and Practice", Elsevier Academic Press, Amsterdam, 2005, pp. 11, 12, 72-75.
Barrosse-Antle, L. E. et al, "Electroreduction of Sulfur Dioxide in Some Room-Temperature Ionic Liquids", Journal of Physical Chemistry C, 2008, 112(9), pp. 3398-3404.
Bartholomew, C. H.,"Fundamentals of Industrial Catalytic Processes", 2nd Edition, Wiley-Interscience, 2006, pp. 382-398, 412-415.
Berezkin, V. G. et al., "Solubility of Some Carrier Gases in Stationary Liquid Phases Used in Gas-Liquid Chromatography", Russian Chemical Bulletin, 1999, 48(5), pp. 914-916.
Berger, A. et al., "Ionic Liquid-phase Asymmetric Catalytic Hydrogenation: Hydrogen Concentration Effects on Enantioselectivity", Tetrahedron Asymmetry, 2001, 12(13), pp. 1825-1828.
Berman, D. A. et al., "Barnacle Electrode: New Tool for Measuring Hydrogen in High Strength Steels", Metal Progress, 1979, pp. 58-61.
Bevenot, X. et al., "Hydrogen Leak Detection Using an Optical Fibre Sensor for Aerospace Applications", Sensors and Actuators B: Chemical, 2000, 67(1-2), pp. 57-67.

Bevenot, X. et al., "Surface Plasmon Resonance Hydrogen Sensor Using an Optical Fibre", Measurement Science and Technology, 2002, 13, pp. 118-124.
Broder, T. L. et al, "Electrochemical Oxidation of Nitrite and the Oxidation and Reduction of NO2 in the Room Temperature Ionic Liquid [C2mim][NTf2]", Journal of Physical Chemistry B, 2007, 111 (27), pp. 7778-7785.
Butler, M. A., "Fiber Optic Sensor for Hydrogen Concentrations near the Explosive Limit", Journal of Electrochemical Society, 1991, 138(9), pp. L46-L47.
Butler, M. A., "Micromirror Optical-fiber Hydrogen Sensor", Sensors and Actuators B: Chemical, 1994, 22(2), pp. 155-163.
Buzzeo, M. C. et al., "Non-Haloaluminate Room-Temperature Ionic Liquids in Electrochemistry—A Review", ChemPhysChem 2004, 5(8), pp. 1106-1120.
Buzzeo, M. C. et al, "Use of Room Temperature Ionic Liquids in Gas Sensor Design," Analytical Chemistry, 2004, 76 (15), pp. 4583-4588.
Buzzeo, M. C. et al., "Elucidation of the Electrochemical Oxidation Pathway of Ammonia in Dimethylformamide and the Room Temperature Ionic Liquid, 1-Ethyl-3-methylimidazolium bis(trifluoromethylsulfonyl)imide" Electroanalysis, 2004,16(11), pp. 888-896.
Buzzeo, M. C. et al., "Voltammetry of Oxygen in the Room-Temperature Ionic Liquids 1-Ethyl-3-methylimidazolium Bis((trifluoromethyl)sulfonyl)imide and Hexyltriethylammonium Bis((trifluoromethyl)sulfonyl)imide: One-Electron Reduction to Form Superoxide. Steady-State and Transient Behavior in the Same Cyclic Voltammogram Resulting from Widely Different Diffusion Coefficients of Oxygen and Superoxide", Journal of Physical Chemistry A, 2003, 107 (42), pp. 8872-8878.
Cai, H.-Y. et al., "Hydrogen Solubility Measurements in Heavy Oil and Bitumen Cuts", Fuel, 2001, 80(8), pp. 1055-1063.
Cai, Q. et al., "Studies on a Sulfur Dioxide Electrochemical Sensor with Ionic Liquid as Electrolyte", Journal of East China Normal University, 2001, 3, 4 pages.
Chao, Y. et al., "Amperometric Sensor for Selective and Stable Hydrogen Measurement", Sensors and Actuators B: Chemical, 2005, 106(2), pp. 784-790.
Choi, W. K. et al., "H2 Gas-Sensing Characteristics of SnOx Sensors Fabricated by a Reactive Ion-Assisted Deposition With/Without an Activator Layer", Sensors and Actuators B: Chemical, 1997, 40(1), pp. 21-27.
Christensen, C., "Hydrogen Monitoring in Geothermal Plants and Oil and Gas Refineries" Nordtest report T4 474, 2001, 36 pages.
Deubelin, et al., "Novel Electrochemical Hydrogen Sensors for Use at Elevated Temperatures", Solid State Ionics 1988, 28-30, pp. 1660-1663.
Devanathan, M. A. V. et al., "The Adsorption and Diffusion of Electrolytic Hydrogen in Palladium", Proceedings of the Royal Society A, 1962, A270, pp. 90-102.
Dolan, M. D., "Non-Pd BCC Alloy Membranes for Industrial Hydrogen Separation", Journal of Membrane Science, 2010, 362(1-2), pp. 12-28.
Dong, S. X. et al., "A Piezoelectric-Sound-Resonance Cavity for Hydrogen Gas Detection", IEEE Transactions on Ultrasonics, Ferroelectrics, and Frequency Control, 2003, 50(9), pp. 1105-1113.
Dong, S. X. et al., "Sound-Resonance Hydrogen Sensor", Applied Physics Letters, 2003, 82(25), pp. 4590-4592.
Ekedahl, L. G. et al, "Hydrogen Sensing Mechanisms of Metal-Insulator Interfaces", Accounts of Chemical Research, 1998, 31, pp. 249-256.
Endres, F. et al., "Air and Water Stable Ionic Liquids in Physical Chemistry", Physical Chemistry Chemical Physics, 2006, 8, pp. 2101-2116.
Fernandez-Prini, R. et al., "Henry's Constants and Vapor-Liquid Distribution Constants for Gaseous Solutes in H2O and D2O at High Temperatures", Journal of Physical and Chemical Reference Data, 2003, 32(2), pp. 903-916.
Finotello, A. et al, "Room-Temperature Ionic Liquids: Temperature Dependence of Gas Solubility Selectivity", Industrial Engineering Chemistry Research, 2008, 47(10), pp. 3453-3459.

(56) References Cited

OTHER PUBLICATIONS

Fukuta, R. et al., "Hydrogen Electrode Reaction in Some Imide-Type Room-Temperature Ionic Liquids", ECS Transactions, 2007, 3(35), pp. 567-576.

Gomes De Azevedo, R. et al., "Thermophysical and Thermodynamic Properties of Ionic Liquids Over an Extended Pressure Range: [bmim][NTf2] and [hmim][NTf2]", Journal of Chemical Thermodynamics, 2005, 37(9), pp. 888-899.

Huang, X-J. et al., "Electroreduction of Chlorine Gas at Platinum Electrodes in Several Room Temperature Ionic Liquids: Evidence of Strong Adsorption on the Electrode Surface Revealed by Unusual Voltammetry in Which Currents Decrease with Increasing Voltage Scan Rates", Journal of Physical Chemistry C, 2008, 112, pp. 19477-19483.

Hughes R. C. et al., "Thin Films of Pd/Ni Alloys for Detection of High Hydrogen Concentrations", Journal of Applied Physics, 1992, 71, pp. 542-544.

Hughes, R. C. et al., "Solid-State Hydrogen Sensors Using Palladium-Nickel Alloys: Effect of Alloy Composition on Sensor Response", Journal of the Electrochemical Society, 1995, 142(1), pp. 249-254.

Inaba, M. et al., "Gas Crossover and Membrane Degradation in Polymer Electrolyte Fuel Cells", Electrochimica Acta, 2006, 51(26), pp. 5746-5753.

Iyer, R.N. et al., "Mechanism and Kinetics of Electrochemical Hydrogen Entry and Degradation of Metallic Systems", Annual Review of Materials Science, 1990, 20, pp. 299-338.

Jacquemin, J. et al., "Solubility of Carbon Dioxide, Ethane, Methane, Oxygen, Nitrogen, Hydrogen, Argon, and Carbon Monoxide in 1-butyl-3-methylimidazolium Tetrafluoroborate Between Temperatures 283 K and 343 K and at Pressures Close to Atmospheric", Journal of Chemical Thermodynamics, 2006, 38(4), pp. 490-502.

Jacquemin, J. et al., "Influence of the Cation on the Solubility of CO2 and H2 in Ionic Liquids Based on the Bis (trifluoromethylsulfonyl)imide Anion", Journal of Solution Chemistry, 2007, 36, pp. 967-979.

James, S. W. et al., "Optical Fibre Long-Period Grating Sensors: Characteristics and Application", Measurement Science and Technology, 2003, 14, pp. R49-R61.

Ji, X. et al., "Mechanistic Studies of the Electro-Oxidation Pathway of Ammonia in Several Room-Temperature Ionic Liquids", Journal of Physical Chemistry C, 2007, 111 (26), pp. 9562-9572.

Jin, X. et al, "Ionic Liquid High-Temperature Gas Sensor Array", Analytical Chemistry, 2006, 78, pp. 6980-6989.

Katsuki, A. et al., "H2 Selective Gas Sensor Based on SnO2", Sensors and Actuators B: Chemical, 1998, 52(1-2), pp. 30-37.

Kumelan, J. et al., "Solubility of H2 in the Ionic Liquid [hmim][Tf2N]", Journal of Chemical and Engineering Data, 2006, 51(4), pp. 1364-1367.

Kumelan, J., "Solubility of the Single Gases H2 and CO in the Ionic Liquid [bmim][CH3SO4]", Fluid Phase Equilibria, 2007, 260(1), pp. 3-8.

Landolt, D., "Corrosion and Surface Chemistry of Metals", EPFL Press, Lausanne, 2007, pp. 477-511.

Leckel, D., "Diesel Production from Fischer-Tropsch: The Past, the Present, and New Concepts", Energy & Fuels, 2009, 23(5), pp. 2342-2358.

Lee, D. et al., "Synthesis, Characterization, and Gas Permeation Properties of a Hydrogen Permeable Silica Membrane Supported on Porous Alumina", Journal of Membrane Science, 2004, 213(1-2), pp. 117-126.

Stapp, P.R., "In situ hydrogenation", report NIPER-434, IIT Research Institute, National Institute for Petroleum and Energy Research, Bartlesville, OK, Dec. 1989, 44 pages.

Neissman, J.G., "Review of processes for downhole catalytic upgrading of heavy crude oil", Fuel Process. Technol., 50, 1997, pp. 199-213.

Todd, R.S et al., "Hydrogen recycling and on-site generation", Industrial Heating 2007, 74, pp. 97-100.

Kopasz, J.P. et al., "Reforming petroleum based fuels for fuel cell vehicles: composition-performance relationships", Jun. 2002 Future Car Congress, Arlington, VA, 8 pages.

Hendricks, N.H. et al., "Synthesis and characterization of fluorinated poly(arylethers): organic polymers for Ic Imd", Mater. Res. Soc. Symp. Proc., 381, 1995, pp. 59-70.

Ohara, S. et al., "Palladium-polyelectrolyte hybrid nanoparticles for hydrogen sensor in fuel cell", Power Sources, 193, 2009, pp. 367-370.

Bohringer, W. et al., "Selective Fischer-Tropsch wax hydrocracking - opportunity for improvement of overall gas-to-iquids processing", Fischer-Tropsch Synthesis, Catalysts and Catalysis (B.H. Davis and M.L. Occelli, eds), Studies in Surface Science and Catalysis 163, 2007, Elsevier, Amsterdam, pp. 345-365.

Sie, S.T. et al., "Conversion of natural gas to transportation fuels via the Shell distillate synthesis process (SMDS)", Catalysis Today, 8, 1991, pp. 371-394.

Cheng, X. et al., "Hydrogen crossover in high- temperature PEM fuel cells", J. Power Sources, 167, 2007, pp. 25-31.

Steynberg, A.P. and Dry, M.E. (eds.), Fischer-Tropsch Technology, Studies in Surface Science and Catalysis 152, 2004, Elsevier, Amsterdam, pp. 503-514.

\* cited by examiner

ELECTROCHEMICAL HYDROGEN SENSOR

CROSS REFERENCE TO RELATED APPLICATION(S)

This application is a continuation of U.S. patent application Ser. No. 14/436,221, filed Apr. 16, 2015, which is a 371 national stage entry of Patent Cooperation Treaty Patent Application No. PCT/IB2013/059370, filed Oct. 15, 2013, which claims the benefit of and priority to U.K. Patent Application No. 1218514.6, filed Oct. 16, 2012. Each of the foregoing applications is incorporated herein by this reference in its entirety.

BACKGROUND

Hydrogen is a colourless, odourless gas which is difficult to detect easily, and is flammable at concentrations above approximately 4 volume percent in air. Hydrogen gas is employed in a wide variety of industrial processes. It serves as fuel in fuel cells, and as a rocket propellant. It is also commonly used in a range of chemical syntheses, for example in the Haber process (converting nitrogen and hydrogen to ammonia in the presence of an iron catalyst) and in a range of hydrogen treatment reactions, such as the hydrogenation of fats and oils, hydrodealkylation, hydrocracking and hydrodesulfurization.

There are a variety of circumstances where it can be desirable to detect the presence of hydrogen and a variety of technologies have been employed for this purpose. Detectors have used oxides (e.g. $SnO_2$), metal-insulator-semiconductor surfaces, polymers, and high-temperature molten salts, and have been based on techniques including optical sensing, acoustic detection, electrochemistry and gas chromatography. However, existing hydrogen sensors commonly have limitations which restrict their use. Some sensors are only suitable for laboratory conditions or require a trained operator. Some sensors cannot be used when other gases are mixed with hydrogen and some sensors cannot be used at elevated temperatures or pressures, such as those commonly found in chemical processes and in underground oil and gas wells.

At present, there are only very few reports of hydrogen sensors used in the upstream oil and gas industry. The concentration of hydrogen in wellbore fluids (oil, water and gas) is not routinely measured. Despite the absence of measurements, there are a number of problems associated with hydrogen, including a reaction with the silica optical fibers used in wellbores (forming SiOH groups that can severely reduce transmission of light through them) and its generation by corrosion reactions (including reaction of $H_2S$ with metals) where it can cause stress corrosion cracking in some steels and alloys.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

One aspect of the disclosed subject matter of this application is a sensor for hydrogen in a fluid medium where the sensor includes a housing that encloses a chamber for electrolyte and which includes a window positioned in an opening in the housing, a quantity of electrolyte within the chamber, the electrolyte being an ionic liquid under the conditions of use of the sensor, and a plurality of electrodes in contact with the ionic liquid electrolyte, wherein the window is permeable to hydrogen to allow hydrogen to pass from the fluid medium under test into the electrolyte.

The sensor may be such that the ionic liquid electrolyte fills the electrolyte chamber within the housing. The ionic liquid may be sealed within the electrolyte chamber.

The fluid medium under test may be a liquid, a gas or a mixture of gas and liquid. Such a sensor can be of simple construction, although the materials used in it are unusual and specialised. Very few, if any, moving parts are required and the sensor can be constructed to operate at temperatures above those of a human environment.

In some circumstances it may be acceptable for the window to allow passage of gases other than hydrogen, for instance if it is desired to measure hydrogen in the presence of an inert gas which will not undergo electrochemical reaction nor interfere with the direct electrochemical oxidation of hydrogen. However, in some forms of this invention, the window may comprise a layer of material which is selectively permeable to hydrogen. Selective permeability to hydrogen enables the sensor to detect hydrogen even in the presence of a greater concentration of another gas which would be able to undergo electrochemical reaction if it entered the ionic liquid electrolyte.

A range of materials can possibly be used for hydrogen separation, including metals, silica, zeolites and polymers. Metals are an attractive choice of material, likely to give the highest levels of specificity whereas polymers can suffer from problems of thermal stability and high permeability to polar molecules, such as water and $CO_2$. For a recent review see Ockwig, N. W. and Nenoff, T. M., "Membranes for hydrogen separation", Chemical Review, 2007, vol. 107, pp. 4078-4110.

A hydrogen permeable window may be a thin layer of material which is selectively permeable to hydrogen, supported on another material which is permeable to hydrogen and also to other gases. The layer which is selectively permeable to hydrogen may be formed of a metal. Thus the window may be a metallic membrane. Metals which can selectively allow passage of hydrogen include vanadium, niobium, tantalum and palladium and alloys containing them.

An issue with metals other than palladium such as niobium, tantalum and titanium is that they have a body centred cubic (bcc) crystal structure that makes then susceptible to stress corrosion cracking. The formation of cracks in a metal membrane can severely reduce separation efficiency as well as threatening the integrity of the hydrogen sensor. In contrast, palladium has a face centred cubic (fcc) crystal structure and does not exhibit stress corrosion cracking. The recent development of bcc alloys has gone some way to reducing their tendency to undergo stress corrosion cracking. For example, see Dolan, M. D., "Non-Pd BCC alloy membranes for industrial hydrogen separation", Journal of Membrane Science, 2010, vol. 362, pp. 12-28.

Palladium may be used alone or alloyed with another metal. Possible are alloys of palladium with copper or with silver. Palladium may provide at least 50% of any alloy. A review of hydrogen permeable palladium membranes is Paglieri, S. N. and Way, J. D., "Innovations in palladium membrane research", Separation and Purification Methods, 2002, vol. 31, pp. 1-169. This membrane may take the form of a thin sheet of metal, which may be palladium or palladium alloy. Such a membrane may be placed on an inert, porous support.

Another possibility for construction of a membrane is that the metal, such as palladium or a palladium alloy, can be vacuum sputtered onto a polymer sheet which is permeable to gases. Sputtering onto a polymer sheet is described in U.S. Pat. No. 4,857,080 and in Athayde et al., Journal of Membrane Science, 1994, 94, p. 299. The polymer sheet may be a polyetherimide or polyetheretherketone (PEEK) or a polysulfone or poly(tetrafluoroethylene) (PTFE) which can in turn be placed on an inert, porous support.

The thickness of hydrogen selective metal or alloy may be no more than 200 μm, possibly no more than 100 μm. If the layer is formed by sputtering onto a polymer sheet it may be no more than 10 μm thick and it may be less than 1 μm in thickness. The range of thickness of hydrogen selective metal may possibly be from 0.1 μm to 200 μm. An inert porous support may be a rigid inorganic material such as silica or alumina and may be at least 1 mm or at least 2 mm thick. Such a material may allow operation at temperatures over 100° C., possibly up to 200° C. or 400° C. Other possibilities for supports are titanium dioxide and some ceramics that do not react with hydrogen (e.g., the material sold by Corning Inc under their trademark MACOR, which is a borosilicate glass matrix containing fluorphlogopite mica). Polymers such as polyether ether ketone (PEEK) or high-density polyethylene may be used, in particular when temperatures are low, such as less than about 125° C. and differential pressures across the membrane system are small, such as less than 70 bar.

The surface of the hydrogen selective membrane opposite to the support may have a gas-permeable protective film applied to it to prevent it from mechanical damage or chemical attack. This protective coating may be a polymer film, for example poly (p-phenyleneterephthalamide) which is available commercially under the trademark KEVLAR or polybenzimidazole (FBI). Such a polymer film can be impregnated with reagents capable of removing compounds that may damage the palladium membrane, such as hydrogen sulfide. For example, the reagent zinc oxide can be dispersed into the protective polymer coating to capture hydrogen sulfide by the formation of zinc sulphide and water.

A protective coating may alternatively be provided by inorganic material deposited on the membrane. This may allow use of the sensor at temperatures which are higher than can be tolerated by an organic polymer.

An ionic liquid, which is used as the electrolyte, is a salt or a mixture of salts with a low melting point so that it exists in a liquid form. The electrolyte may be in liquid form at 20° C. (so that it can be referred to as a room temperature ionic liquid) but if the sensor is intended to be operated at a higher temperature, the electrolyte may be a salt or mixture of salts which melts above 25° C. and is in a liquid state at the temperature of use of the sensor.

For example, if the sensor is to be used at a temperature above 100° C., the mixture of salts might melt to liquid form at a temperature in a range from 40° C. to 90° C. However, the ionic liquid electrolyte may be liquid at temperatures below ambient, such as temperatures down to −10° C. or below, which will help avoid any issues arising from solidification of the electrolyte during transportation in a cold climate.

An ionic liquid electrolyte may comprise one or more salts in which the anion or the cation or both of them are organic compounds containing carbon and other atoms which are covalently bonded. The electrolyte may be anhydrous but if it does contain water the amount of water may be less than 10% by weight, possibly less than 5% or even 1% by weight.

The ionic liquid may be insoluble or have low solubility in water. In this case some water may dissolve in the ionic liquid, but the ionic liquid is not miscible with water at any and all proportions. We have found that a sensor as disclosed here may operate satisfactorily when some water is dissolved in the ionic liquid electrolyte, so that it may be unnecessary to dry the ionic liquid to an anhydrous condition. The water concentration in the ionic liquid may possibly be no more than 1% by weight.

Ionic liquids are generally not volatile and a non-volatile ionic liquid may be used here as electrolyte. Measurements reported in the literature indicate that ionic liquids can display considerable thermal stability. The ionic liquid electrolyte may be thermally stable to the extent that not more than 1% of the salt decomposes on heating for 20 hour under vacuum or in an inert gas atmosphere at temperatures up to 250° C. and possibly even up to 350° C. There are literature reports that ionic liquids display very good thermal stability. For instance Seeberger et al., "Prediction of long-term stability of ionic liquids at elevated temperatures", Phys. Chem. Chem. Phys., 2009, vol. 11, pp. 9375-9381 have shown that the ionic liquid 1-butyl-3-methylimidazolium bis(trifluoromethylsulfonyl)imide has such a low rate of thermal degradation in a closed system that the time for loss of 1% is over a year at 250° C.

The sensor may be part of test apparatus which also includes means for applying electrical potential to the electrodes and measuring current flow. A potentiostat may be used for this purpose and may be computer controlled. More specifically, measurements may be amperometric measurements (i.e. measurements of current flow) under conditions of known and/or fixed potential.

In another aspect there is disclosed a process for determining hydrogen in a fluid medium, and which includes contacting the fluid medium with a sensor which comprises a housing which encloses a chamber for electrolyte and which includes a hydrogen-permeable window positioned in an opening in the housing; having a quantity of electrolyte, which is an ionic liquid, in the chamber, and a plurality of electrodes in the chamber in contact with the ionic liquid electrolyte, allowing hydrogen to pass through the window from the fluid medium into the electrolyte, applying electrical potential to the electrodes, and measuring current flow.

The sensitivity of the hydrogen sensor can be controlled by the structure and surface area of the working electrode. Liang et al., "Controllable synthesis of hollow hierarchical palladium nanostructures with enhanced activity for proton/hydrogen sensing", Journal of Physical Chemistry C, 2008, 112, pp. 338-344 have shown that the use of a nanoparticulate palladium working electrode can significantly increase the oxidation and reduction currents measured by conventional macro- or micro-electrodes for a given concentration of hydrogen or hydrogen ions in solution.

As already mentioned, the fluid medium which is examined for hydrogen content may be liquid, or gaseous or a mix of the two. It may be under pressure and at a temperature above ambient temperature of a human environment. The partial pressure of hydrogen gas may exceed 1 bar and reach values of up to 100 bar especially if the fluid medium is below ground. Temperature may range up to 200° C. possibly even up to 400° C. If a sensor is to be used at temperatures above 200° C. it may be constructed entirely from inorganic materials.

A hydrogen sensor as set out above may be used in a number of applications. One of these is in a downhole tool for measuring the content of hydrogen in a subterranean fluid. Such subterranean fluid may be hydrocarbon as oil or natural gas, water, brine or a mixture of these. In particular it may be crude oil mixed with brine, a mixture which is encountered in many oil reservoirs.

Subterranean conditions encountered in oil exploration and production may be a hostile environment in which high pressure and temperature are encountered along with a content of carbon dioxide and/or hydrogen sulphide. In such circumstances the hydrogen-permeable membrane may carry a protective layer which is inorganic material deposited thereon.

When used in a downhole tool, a sensor may be heated to operate at a controlled temperature which is above the prevailing temperature of the fluid surrounding the tool. This can enable measurements to be made at a fixed temperature, thus simplifying calibration of the tool. Heating also reduces the viscosity of ionic liquid and allows equilibrium concentrations of hydrogen to be reached more quickly.

A further application is monitoring a metal, which may be steel or an alloy, for dissolved hydrogen generated by contact with acid. For this application the sensor may be attached to a metal test piece (a so-called coupon) or it could be attached to some other item of metal. For example the sensor could be located in a tool so as to monitor hydrogen dissolving in the metal of the tool as a result of corrosion of the tool.

Another application is monitoring the enclosure of an optical fiber for the presence of hydrogen.

Yet further applications are as a hydrogen sensor in equipment carrying out a chemical or electrochemical process which involves hydrogen gas as a feedstock, product or intermediate so that the process consumes hydrogen, produces hydrogen, or both produces and consumes hydrogen. There are a considerable range of processes which consume and/or produce hydrogen but one specific area is in gas-to-liquid processes converting natural gas to a liquid product. Hydrogen sensors as disclosed here may be used in the process plant, and may in particular be used when the equipment is constructed to carry out the process on a small industrial scale so that laboratory facilities for monitoring operations are unlikely to be available.

Another application to a chemical process is monitoring hydrogen leakage in a fuel cell which uses hydrogen to generate electricity. There are a number of types of fuel cell which can use hydrogen. A sensor as disclosed here may be used in polymer electrolyte membrane fuel cells but also in other types include solid oxide and phosphoric acid fuel cells.

DETAILED DESCRIPTION

Figure 1:
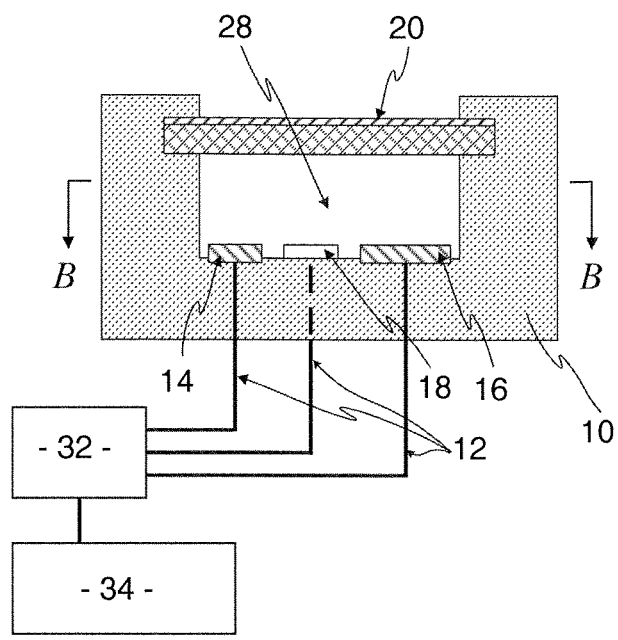
FIG. 1 is a schematic cross-sectional view of a hydrogen sensor on line A-A of FIG. 2.

FIG. 1 shows an embodiment of hydrogen sensor in cross-section. The sensor is shaped as a bulkhead compartment. It has a body 10 with a cylindrical dish shape including a flat base. The body 10 is made from an electrically insulating material and in this embodiment this material is a machinable ceramic. A suitable ceramic is a material made by Corning Inc., Corning, N.Y. and sold under their trademark MACOR. The manufacturer describes it as fluorphlogopite mica (approximately 55%) in a borosilicate glass matrix. Other possible materials are high temperature polymers such as polyetheretherketone (PEEK).

Three circular electrodes are provided on the base of the body 10 and connections 12 to each of these electrodes extend through the material of the body 10. These electrodes are a working electrode 14, a counter electrode 16 and a reference electrode 18 arranged in a layout shown by FIG. 2 which puts the counter and reference electrodes at similar distances from the working electrode 14. Suitable materials for the working electrode 14 include platinum and palladium. The reference electrode 18 may be silver and the counter electrode 16 may be platinum. All three electrodes 14, 16, 18 are sufficiently large to be classed as macroelectrodes. In this embodiment, the working electrode 14 has a surface area of approximately 1 mm$^2$, while the counter electrode 16 is larger than the working electrode 14 and has a surface area of approximately 3 mm$^2$ and the reference electrode 18 has a surface area of approximately 0.2 mm$^2$.

When the sensor is used to detect low concentrations, such as in leak detection and the dissolved hydrogen content in the ionic liquid is less than about 10$^{-4}$ molar, then the working electrode can be composed of palladium nanoparticles, such as those described by Liang et al., "Controllable synthesis of hollow hierarchical palladium nanostructures with enhanced activity for proton/hydrogen sensing", Journal of Physical Chemistry C., 2008, vol. 112, pp. 338-344.

Silver in an ionic liquid is not a standard reference electrode and may not maintain an absolute value of potential. Nevertheless, it is sufficiently stable to allow electrochemical voltammetry and it is sometimes referred to as a pseudo reference. If desired, a metallocene such as ferrocene may be dissolved in the ionic liquid so that the electrochemical signal includes the reversible oxidation of the metallocene as an internal standard.

A window 20 which is permeable to hydrogen is sealed to the sensor body 10 so as to fit in the mouth of the dish shape. In this embodiment the hydrogen-permeable window 20 is parallel to the base of the body 10 but spaced from it. As shown by the enlarged view in FIG. 3, this window 20 has a thin membrane 22 which is selectively permeable to hydrogen supported on a disc 24 of porous inert material such as alumina. This disc 24 is not specific in its porosity and would allow passage of other gases, if any other gases happened to be present.

The membrane 22 is a thin sheet of palladium metal or an alloy of palladium, such as palladium alloyed with approximately 40% copper. The sheet may possibly be 0.01-100 µm in thickness. The supporting disc 24 may have a thickness of 0.1-10 mm, depending on the expected pressure of the test fluid in contact with window 20.

In an alternative construction the membrane 22 is formed by palladium sputtered onto a polymer membrane or porous polymer support which may be a polyetherimide, polyether ether ketone (PEEK), polysulfone or polytetrafluoroethylene (PTFE). This polymer membrane is placed on the inert porous support 24.

The membrane 22 is coated with a thin polymer film 25, for instance a film of poly(para-phenylterephthalamide) which is available under the trade name Kevlar or polybenzimidazole (PBI) to protect it from mechanical damage or chemical attack. The polymer coating 25 may be impregnated with one or more scavenger reagents to removing compounds harmful to the palladium membrane. For example zinc oxide can be dispersed into the protective polymer coating to capture hydrogen sulphide by the formation of zinc sulphide and water.

Figure 2:
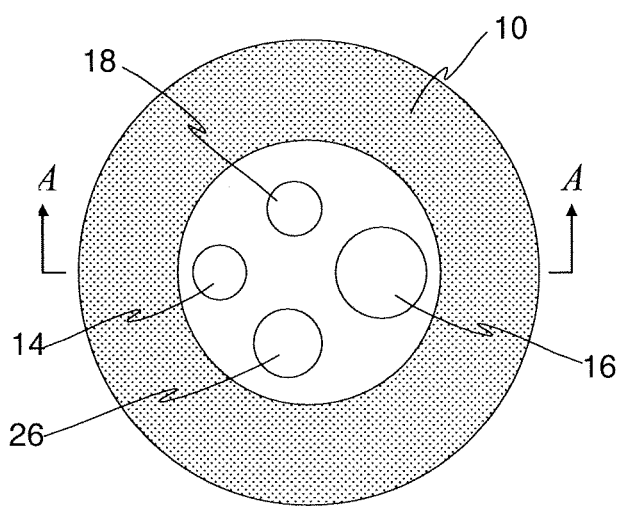
FIG. 2 is a cross-sectional view on line B-B of FIG. 1.

As indicated in FIG. 2, a combined temperature and pressure sensor 26 is also provided on the base of the body 10 to measure temperature and pressure within the enclosed interior chamber 28 bounded by the body 10 and the window 20.

This chamber 28 is filled with an electrolyte which is an ionic liquid. In this embodiment the electrolyte is liquid at ambient temperatures of 20-25° C. and remains liquid down to −10° C. Ionic liquids are described in a number of documents. A discussion by Silvester et al. is at Zeitschrift fur physikalische Chemie, 2006, vol. 220, pp. 1247-1274.

Some examples of ionic liquids which may be used are 1-butyl-3-methylimidazolium bis(trifluoromethylsulfonyl) imide, 1-ethyl-3-methylimidazolium bis(trifluoromethyl-sulfonyl)imide, 1-butyl-3-methylimidazolium trifluoromethanesulfonate, 1-butyl-3-methylimidazolium tetrafluoroborate, 1-butyl-3-methylimidazolium hexafluorophosphate, 1-hexyl-3-methylimidazolium tris(pentafluoroethyl)trifluorophosphate, N-butyl-N-methylpyrrolidinium bis(trifluoromethylsulfonyl)imide, 1-hexyl-3-methylimidazolium chloride, 1-butyl-3-methylimidazolium nitrate, Hexyltriethylammonium bis(trifluoromethylsulfonyl)imide, and Tetradecyltrihexylphosphonium bis(trifluoromethylsulfonyl)imide.

It will be appreciated that the ionic liquids listed above have cations which are organic molecules. They contain alkyl groups and/or an organic ring. In some of the above liquids the anions incorporate carbon atoms as trifluoromethyl groups. Ionic liquids which contain bis(trifluoromethylsulfonyl)imide or hexafluorophosphate anions are generally insoluble in water while the solubility of water in them is low, such as less than 0.5% possibly less than 0.1% by weight. Thus, ionic liquids with these anions have a relatively low atmospheric water uptake. The ionic liquid used in the chamber 28 may be one of the above liquids with a bis(trifluoromethylsulfonyl)imide or hexafluorophosphate anion.

The electrodes 14, 16, 18 are connected by connections 12 to a potentiostat 32 for applying potential to the electrodes and measuring current flow. The potentiostat 32 is connected to a controlling computer 34 which receives and records values of current flow at the applied potential.

In use the sensor is brought into contact with the fluid medium to be examined so that this is in contact with the exterior face of the hydrogen-permeable window 20. Hydrogen dissolved in this fluid medium can diffuse through the membrane and the support into solution in the ionic liquid electrolyte. Hydrogen can pass through the membrane in both directions and an equilibrium will be reached with concentration in the electrolyte proportional to the concentration in the fluid medium which is being examined. Electrical potential is applied to the electrodes and the current flow associated with electrochemical oxidation of hydrogen

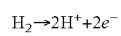

$$H_2 \rightarrow 2H^+ + 2e^-$$

is measured. This current flow is a measure of the hydrogen concentration in the ionic liquid electrolyte and can be used to determine the concentration in the fluid medium which is being examined after calibration of the sensor to determine the relationship between equilibrium concentrations employed in the external fluid medium being examined and in the ionic liquid in the interior chamber 28 of the sensor.

Example 1

In this Example 1, experiments were carried out using an ionic liquid and hydrogen gas, without a membrane, in order to demonstrate the electrochemistry.

Metal wire electrodes were sealed into a small trough in the base of a plastic dish provided with inlets and outlets for the flow of gas. The working electrode was a platinum disc of approximately 0.5 mm diameter and was shown by electrochemical calibration to have a diameter of 530 µm. The reference electrode was a silver wire of approximately 0.5 mm diameter and the counter electrode was a platinum wire also of approximately 0.5 mm diameter.

The ionic liquid 1-butyl-3-methylimidazolium bis(trifluoromethylsulfonyl)imide (abbreviation [$C_4$mim][$NTf_2$]) from QUILL, Queens University, Belfast, UK, was additionally dried and stirred under vacuum at 70° C. for 24 hours. 30 µL of this ionic liquid was pipetted into the trough to cover the three electrodes and an air-tight lid was placed on the dish. Hydrogen gas was passed through from inlet to outlet, so that the ionic liquid was in direct contact with the hydrogen. This was continued for about ten minutes to ensure complete equilibrium between the gas and liquid phases before cyclic voltammetry was carried out. (However, it was noted that the same electrochemical results were obtained if hydrogen was passed through for less than a minute, indicating that equilibrium between the gas and liquid phases was achieved in this short time).

Figure 4:
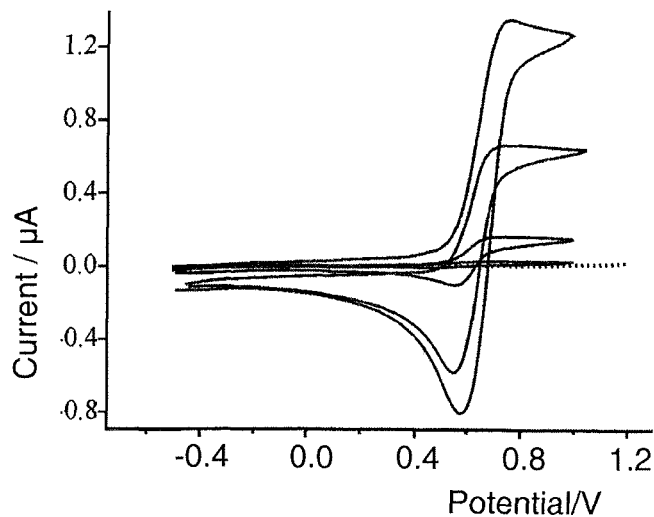
FIGS. 4 and 5 show results of cyclic voltammetry with microelectrodes in Example 1.
Figure 5:
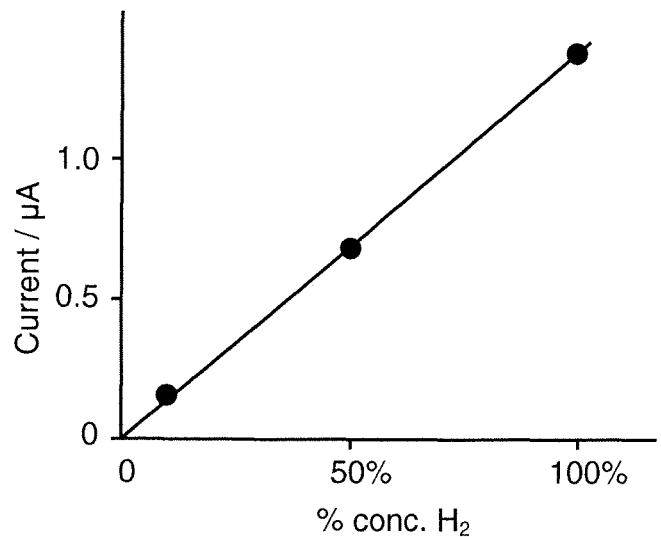

The electrodes were connected to a µ-autolab II potentiostat (Ecochemie, Netherlands) which was used to carry out cyclic voltammetry measurements at room temperature of 22° C., varying the potential applied to the working electrode, relative to the silver reference electrode, between −0.5 volt and +1.1 volt and recording the current flow as the potential was varied. The scan rate was 100 mVsec$^{-1}$. This procedure was then repeated using mixtures of 1%, 10% and 50% hydrogen in nitrogen. Results are shown in FIG. 4. The voltammetric wave can be seen to contain an oxidation peak at about +0.7 volt. A plot of the peak current against hydrogen concentration is shown in FIG. 5 and shows a linear relation of electric current to hydrogen concentration.

Figure 6:
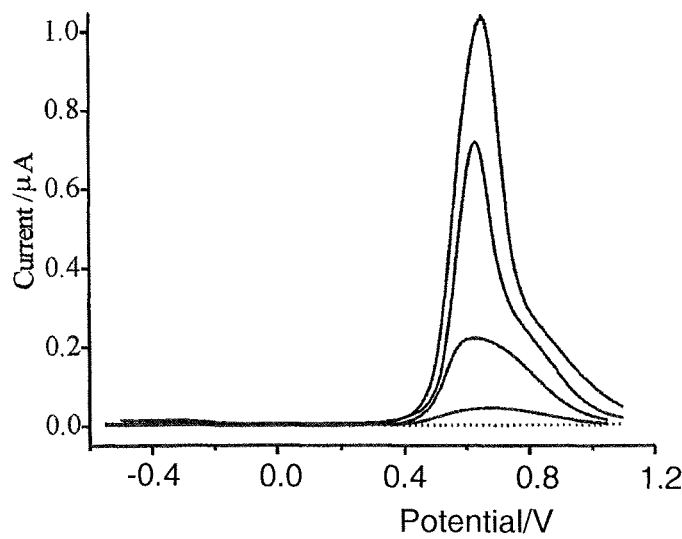
FIG. 6 shows results of square wave voltammetry with microelectrodes in Example 1.

Square wave voltammetry was also carried out over the same voltage range and the results are shown in FIG. 6. At each of the hydrogen concentrations, a large and sharp peak at about +0.7 volt relative to the silver reference was observed, which, even at the lowest concentration of hydrogen (1%), was seen to be separated from the baseline (blank ionic liquid with no exposure to hydrogen) shown as a dotted line.

Example 2

Again, experiments were carried out without a membrane, in order to demonstrate the electrochemistry. A 1.6 mm diameter Pt macrodisk working electrode, a reference electrode of 0.5 mm diameter silver wire, and a Pt coil counter electrode were placed in a glass vial and covered with about 1.5 ml of ionic liquid (same liquid as previous example) open to the atmosphere. Hydrogen gas or mixtures of hydrogen and nitrogen were bubbled directly into the ionic liquid for about 15 minutes to ensure complete equilibration. Cyclic and square wave voltammetry were then carried out as in the previous example.

Figure 7:
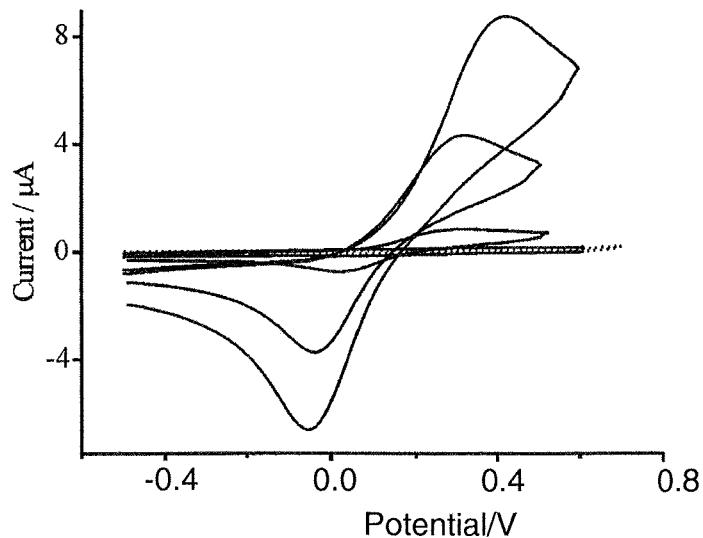
FIGS. 7 and 8 show results of cyclic voltammetry with macrodisc electrodes in Example 2.
Figure 8:
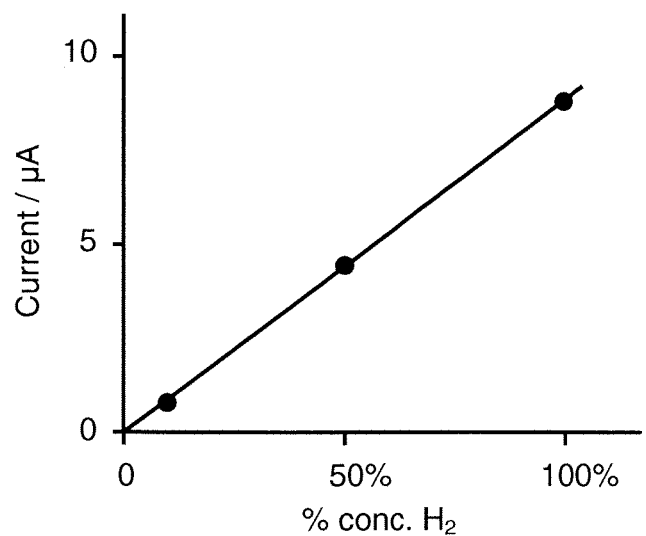
Figure 9:
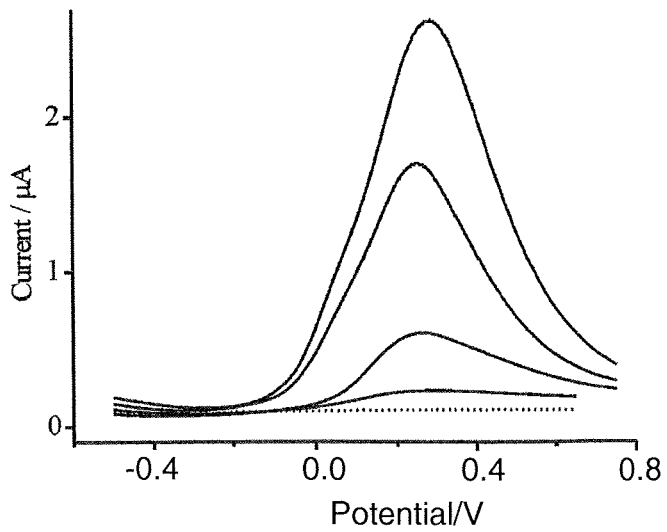
FIG. 9 shows results of square wave voltammetry with macrodisc electrodes in Example 2.

Cyclic voltammetry results are shown in FIG. 7. A broader oxidation peak than in FIG. 4 was observed, with a reduction peak that was separated from the oxidation peak by ca. 0.5 volt at 100% hydrogen, suggesting more electrochemical irreversibility on the larger electrode. Again the peak current is proportional to hydrogen concentration as shown by FIG. 8 which is a plot of current against hydrogen concentration. The square wave voltammetry results in FIG. 9 show a large peak at approx. +0.3 volt (vs. Ag) which increased progressively with increasing concentrations of hydrogen.

The above procedure was repeated using the same ionic liquid which had been saturated with water. The saturation quantity of water in this ionic liquid was under 0.5% by weight. However, no significant differences in the current responses were observed.

Wellbore Tool

One application of the hydrogen sensor is in a tool which is temporarily placed in a wellbore. The hydrogen sensor can then be operated to determine the concentration of hydrogen in wellbore fluid.

Figure 10:
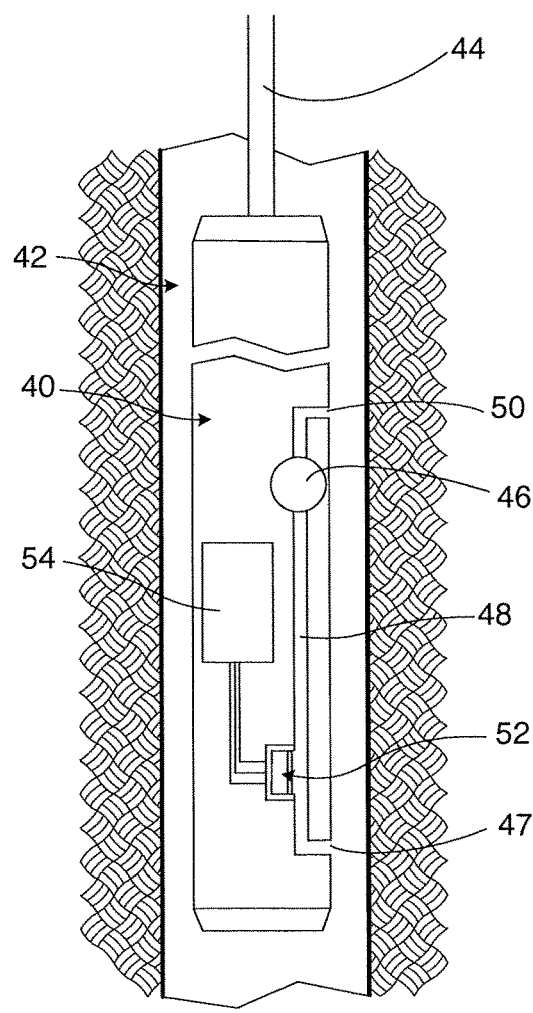
FIG. 10 is a schematic cross-section of a downhole tool in a wellbore.

FIG. 10 is a schematic view of a tool 40 temporarily lowered into a wellbore 42 by a wireline cable 44. The tool incorporates a pump 46 which draws in fluid from outside the tool through inlet 47 along a flowline 48 to an outlet 50. The tool 40 may also have means (not shown) to collect samples of the wellbore fluid and store them under pressure until the tool is returned to the surface.

Figure 3:
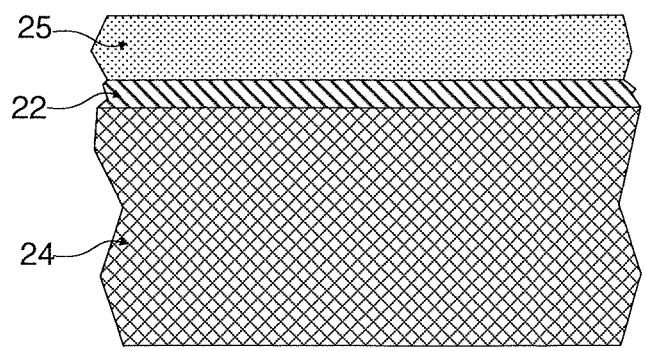
FIG. 3 is an enlarged cross-section of part of the hydrogen permeable window of the sensor of FIG. 1.
Figure 11:
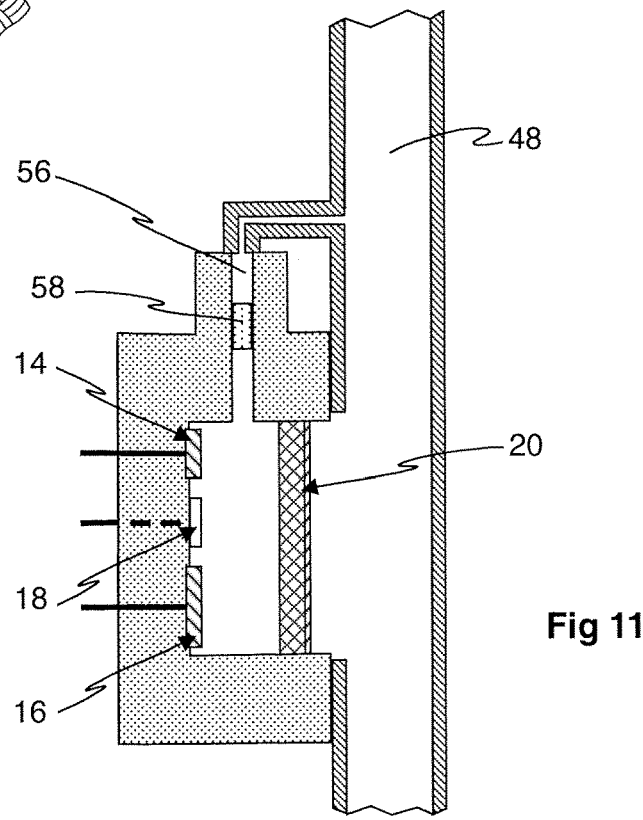
FIG. 11 is a cross-section of a sensor attached to the flowline of the tool of FIG. 10.

A hydrogen sensor 52 constructed as in FIGS. 1 to 3 is located on the flowline 48 so that the hydrogen-permeable window 20 of the sensor is exposed to the fluid in the flowline 48. FIG. 11 shows this in more detail.

The sensor 52 and the pump 46 are connected to an electronics package 54 which incorporates a potentiostat and a controlling computer which operates the potentiostat to make measurements and which records the results. The electronics package may communicate results to the surface via the wireline cable 44.

For use, when the tool 40 is at a chosen position in the wellbore, the pump 44 is used to draw fluid along the flow line 48 hydrogen passes in both directions through the permeable window of the sensor 52 and hydrogen concentration in the ionic liquid in the sensor equilibrates with hydrogen concentration in the fluid in the flowline 48. The sensor 52 is operated to determine peak current flow during a voltammetric sweep and this is used to determine the hydrogen concentration in the wellbore fluid around the tool 40.

Pressure inside the sensor 52 is matched to pressure in the flow line 48 by means of a communicating passage 56 which includes a floating piston 58 or other physical barrier which prevents mixing of liquids but allows the hydraulic pressure in the flow line 48 to be transmitted to the ionic liquid in the sensor 52.

It will be appreciated that the diffusivity of hydrogen in the palladium membrane of the window 20 (and hence the rate at which hydrogen passes through the membrane) does not affect the equilibrium measurement of hydrogen concentration. Any changes in the transport properties of the membrane caused by changes in temperature, or by physical fouling (for example accumulation of solid particles on the hydrogen-permeable window) or even reaction of some of the palladium metal with hydrogen sulfide or other sulfur-bearing compounds in the borehole fluids do not change the equilibrium response of the sensor, although the time taken to reach equilibrium may be increased. Equilibrium hydrogen concentration in the ionic liquid will be observed as constant oxidation current in a succession of measurements.

If desired, the tool 40 may include an electrical heating coil (not shown) around the sensor body. This may be used to raise the temperature of the sensor to a constant temperature which is above the temperature in the wellbore. This will reduce the viscosity of the ionic liquid, thereby shortening the time to reach an equilibrium hydrogen concentration, and will enable the measurement of hydrogen concentration to be made at constant temperature, which can simplify the calibration of the sensor.

The tool 40 may include other sensors for examining fluid in the flowline 48. In particular it may contain a sensor for hydrogen sulphide and thiols. Measurement of the concentration of hydrogen in wellbore fluids may be augmented by a measurement of the concentration of hydrogen sulfide if it is suspected that the hydrogen results from corrosion of coupon s by hydrogen sulphide. One example of a suitable wellbore hydrogen sulfide sensor has been disclosed in U.S. Pat. No. 6,939,717 and U.K. Patent No. GB 2,397,651.

Example 3

To exemplify use in a downhole tool, a sensor constructed as in FIGS. 1 to 3 was used to determine the hydrogen concentration in a sample of a light oil produced from a permeable formation at a temperature of 130° C. and a total pressure of 650 bar (65 MPa). The ionic liquid used in the sensor was 1-hexyl-3-methylimidazolium bis(trifluoromethylsulfonyl)imide, commonly abbreviated to [hmim][NTf$_2$]. The sensor was placed in contact with the oil at a temperature of 130° C. and a pressure of 650 bar.

Cyclic voltammetry was used to determine the concentration of hydrogen dissolved in the ionic liquid. Measurements were repeated until the peak current from the cyclic voltammetry measurement reached a constant value. This value of peak current corresponded to a dissolved hydrogen concentration of 0.0557 moles per kilogram of ionic liquid. Using data presented by Kumelan et al. in Journal of Chemical & Engineering Data, 2006, vol. 51, p. 1364, this hydrogen concentration of 0.0557 moles per kilogram of ionic liquid at a temperature of 130° C. was calculated to correspond to a partial pressure of hydrogen gas of 30 bar. Using extrapolated data presented by Gomes de Azevedo et al. in Journal of Chemical Thermodynamics, 2005, vol. 37, pp. 888-899, the density of [hmim][NTf2] at a temperature of 130° C. and a total pressure of 650 bar was taken to be 1390.2 grams per liter, and therefore the mole fraction of hydrogen dissolved in the ionic liquid is 0.0243. For a typical light oil with a reported mean molar mass of 250 g/mole, a partial pressure of hydrogen of 30 bar has been reported in the same paper by Gomes de Azevedo et al. to correspond to a dissolved hydrogen concentration of 0.1176 moles per kilogram of oil at a temperature of 130° C.

A concentration of 0.1176 moles per kilogram of oil corresponds to a hydrogen content of 235 mg per kilogram or 235 ppm. This concentration can be used to assess the impact on the metals used in the completion and tubing (e.g., stress corrosion cracking) and on other components, such as optical fibers used for temperature measurements and telemetry when the oil is produced.

Corrosion Monitoring

The generation of hydrogen is a common feature of corrosion reactions involving metals and the hydrogen so generated can further damage some metals by causing stress cracking. The rate of hydrogen production by corrosion reactions and the concentration of hydrogen dissolved in metals are valuable parameters in determining corrosion rates and the potential for the failure of metal components by hydrogen-induced stress cracking.

Figure 12:
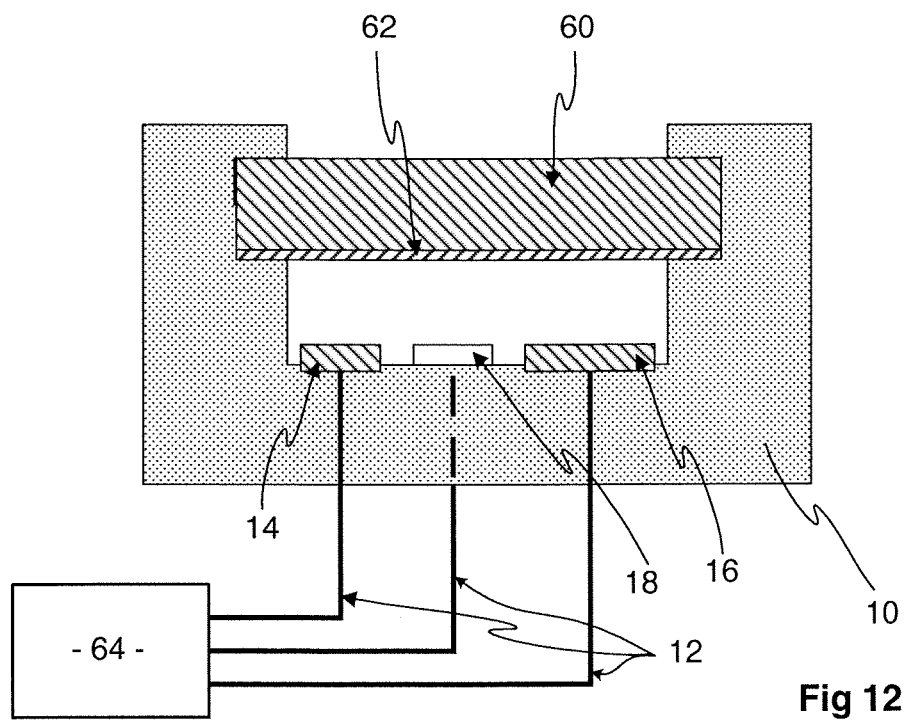
FIG. 12 is a schematic cross-sectional view, similar to FIG. 1, for a sensor used as a corrosion monitor.

FIG. 12 shows a sensor used to monitor corrosion of a test piece, a so-called coupon. The sensor is generally as shown in FIGS. 1 to 3, but the hydrogen-permeable window 20 has been replaced by a disc-shaped coupon 60 of metal to be tested for corrosion. A palladium membrane 62 is brazed to the coupon 60. In this example the metal coupon was duplex stainless steel 22Cr, which contains 22 weight percent chromium, 13 weight percent nickel, 5 weight percent manganese and 3 weight percent molybdenum. The metal coupon 60 was 4 cm in diameter and 4 mm in thickness and was brazed to a palladium disk 62 of 100 µm thickness. The ionic liquid in the electrochemical cell was 1-hexyl-3-methylimidazolium bis(trifluoromethylsulfonyl)imide ([hmim][NTf2]).

The sensor was placed in the completion of a producing well together with an electronics package 64 to carry out cyclic voltammetry measurements at regular intervals and transmit the results to the surface. The well was producing both oil and water and the average values of the hydrostatic pressure and temperature of the fluids in the vicinity of the completion were 490 bar and 118° C., respectively.

The hydrogen sensor initially detected a concentration of 0.0021 moles of hydrogen per kilogram of ionic liquid. The metal coupon was exposed to wellbore fluids and corrosion led to the production of hydrogen, some of which dissolved in the coupon and migrated through the coupon and the palladium membrane into the ionic liquid.

An issue with any method of measuring the hydrogen generated by a surface (corrosion) reaction is where the measurement is made and what fraction of the hydrogen generated reaches the measurement transducer. In the particular geometry presented in this example, the hydrogen is measured after dissolution in the coupon and diffusion through it. Some fraction of the hydrogen generated by the corrosion reaction can be expected to dissolve in the metal of the coupon while the remainder will dissolve in the fluid in contact with the coupon at the exterior of the sensor and be swept away. It may not be possible to assume equilibrium distribution of hydrogen between the water and the metal but experiments can be done to determine the partition of hydrogen between the metal and water as a function of the Reynolds number of the flow of the water.

Over a period of several months of operation the hydrogen sensor with attached stainless steel coupon showed a gradual increase in the hydrogen concentration in the ionic liquid from 0.0021 to 0.0028 moles of hydrogen per kilogram of ionic liquid. This corresponded to an increase in the partial pressure of hydrogen in the sensor from 1.20 bar to 1.58 bar. This showed that there was also an increase in concentrations of hydrogen dissolved in the stainless steel coupon and the water adjacent to it. The increased hydrogen contents of the metal coupon and the water in contact with the coupon are indicative of a corrosion reaction at the surface of the steel coupon and that the metals of similar composition in the well are likely to be undergoing similar corrosion reactions.

If it suspected that hydrogen is being generated at other locations in the well to such an extent that there is an increasing hydrogen concentration in the produced fluids at the exterior of the sensor, then a second hydrogen sensor can be deployed in the wellbore, e.g., on a production logging tool, to monitor the concentration of hydrogen in this fluid.

(a) Monitoring the Performance of Wellbore and Subsea Optical Fibre Systems

The glass used in optical fibres deployed in wellbores to measure temperature can interact with hydrogen (see for instance Stone J in Journal of Lightwave Technology, 1987, vol. 5 p. 712) and reduce the transmissivity of the glass in the near-infrared and visible spectral regions. Interactions which have been identified are the dissolution of hydrogen in the glass and the reaction of hydrogen with certain Si—O or Ge—O defects to form Si—OH and Ge—OH groups. The latter are a permanent change. Both the dissolved hydrogen and the Si—OH and Ge—OH groups absorb radiation in the near-infrared spectral region and hence reduce transmissivity.

A valuable component of predicting the performance of an optical fibre system in a wellbore or subsea environment is to measure the partial pressure (or concentration) of hydrogen, irrespective of its origin.

Figure 13:
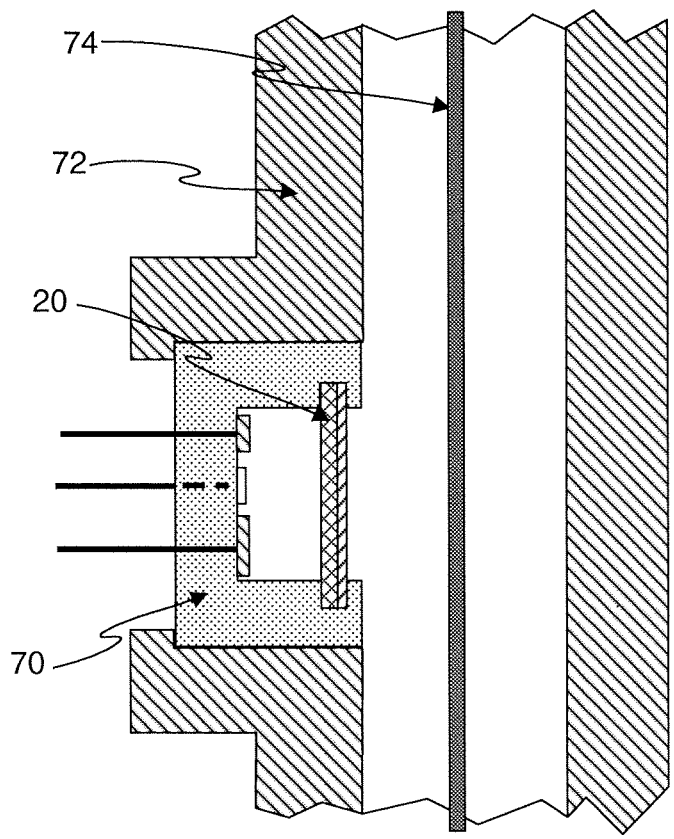
FIG. 13 is a schematic cross-section of a hydrogen sensor monitoring a fiber optic cable.

FIG. 13 shows a schematic of a small hydrogen sensor 70 fitted to a metal tube 72 containing an optical fibre 74. The fibre 74 is deployed in a producing oil well and is used as a temperature sensor connected to a temperature detection system located on the surface to determine the temperature profile of the well. The optical fibre is silica (diameter 125 µm) with a polyamide coating (125 µm thickness) and the tube 72 is a stainless steel tube (6.25 mm external diameter, 3.00 mm internal diameter) containing a silicone oil. Fitting the sensor 70 to the tube 72 can be done by placing the sensor into a modified T-piece fitting, such as the well-known Swagelok fittings used for high pressure tubing connections: details of this are not shown. The electrochemical sensor is generally of the construction shown in FIGS. 1 to 3. The ionic liquid in the interior chamber of the sensor is exposed to the silicone oil in the tube containing the optical fibre by means of a hydrogen-permeable window 20 which is a palladium membrane on an inert, porous support. The surface of the palladium membrane in contact with the silicone oil may be coated with a protective polymer layer 25 as in FIG. 3.

Example 5

The hydrogen sensor 70 was located at a position in the well where the ambient temperature was 182° C. as determined by the fibre optic distributed temperature sensor. The ionic liquid in the hydrogen sensor was 1-hexyl-3-methylimidazolium bis(trifluoromethylsulfonyl)imide ([hmim][NTf2]). The working and counter electrodes were platinum; a silver pseudo reference electrode was used. At this temperature the sensor measured a hydrogen concentration of 0.0050 moles of hydrogen per kilogram of ionic liquid (10.0 ppm), which corresponds to a partial pressure of hydrogen gas of 2.30 bar. Using data on the solubility of hydrogen gas in silicone oil from Berezkin et al., Russian Chemical Bulletin, 1999, vol. 48, pp. 914-916, the corresponding concentration of hydrogen gas dissolved in the silicone oil was calculated to be 0.0178 moles of hydrogen per liter of silicone oil or 42 ppm and using data from Lee et al., Journal of Chemical Physics, 1962, vol. 36, pp. 1062-1071, the concentration of hydrogen dissolved in the glass was estimated to be $4.95 \times 10^{-7}$ moles of hydrogen per cm$^3$ of glass or 0.37 ppm.

Chemical Processes

There are a number of chemical processes which consume or generate hydrogen or in which hydrogen is an intermediate product so that the process both generates and consumes hydrogen. A sensor as described above may be incorporated in a process plant carrying out such a process.

Examples of such processes include processes for converting natural gas, which usually is predominantly methane, into liquid fuels and chemical products via the formation of synthesis gas (a mixture of hydrogen and carbon monoxide). The synthesis gas (frequently termed syngas) is generated within the gas-to-liquid process by reforming or by the partial oxidation of natural gas (predominantly methane). For example, the partial oxidation of methane (CH$_4$) to produce syngas can be described by:

$$CH_4 + 0.5O_2 \rightarrow 2H_2 + CO$$

The syngas so formed can be further reacted to generate useful chemical products. One such reaction is the Fischer-Tropsch reaction, which can be described in simplified form by the conversion of syngas to alkanes and water $$2nH_2 + nCO \rightarrow C_nH_{2n} + nH_2O$$

where C$_n$H$_{2n}$ represents the mixture of alkanes formed by the Fischer-Tropsch reaction. A critical aspect of the Fischer-Tropsch reaction is the H$_2$/CO ratio and the effects of variation of this ratio on the products from the Fischer-Tropsch reaction are well known (see for instance Bartholomew and Farrauto "Fundamentals of Industrial Catalytic Processes", 2nd Edition, 2006, Wiley-Interscience, pp. 412-415). A second reaction involving the conversion of syngas to chemical products is the well-known methanol synthesis reaction discussed in the same book, at pp. 382-398.

$$CO + 2H_2 \rightarrow CH_3OH$$

Methanol can also be synthesised using a mixture of hydrogen and carbon dioxide (CO$_2$)

$$CO_2 + 3H_2 \rightarrow CH_3OH + H_2O$$

noting that water is also produced by the reaction. The methanol synthesis reaction is therefore one method of using natural gas containing significant concentrations of CO$_2$ which may otherwise have little or no economic value.

Chemical processes which create and/or consume hydrogen may be carried out in large-scale fixed industrial plant. The sensors disclosed herein may be used in such process plant. However, it is also known to carry out such chemical processes on a smaller industrial scale and the process plant may then be dimensioned and constructed to be transportable by road vehicle so that the plant can be taken to a natural gas source and taken elsewhere if the flow of natural gas diminishes.

While large scale chemical process plants are able to absorb the cost of expensive process analytical equipment, such as gas chromatographs and mass spectrometers, and skilled operators to monitor the concentration of hydrogen, the economic viability of small scale systems may make it very desirable that the process plant can be manufactured and operated economically, with minimal (or even no) operator personnel and low cost components. The sensors disclosed herein may be advantageous in smaller scale process plant utilised at sites where analytical laboratories and/or trained laboratory staff are not available.

Process plant for conversion of natural gas to another product and/or for upgrading the natural gas stream by converting part of the gas stream of another product, is disclosed in U.S. Patent Publication Nos. US2008/0262110, US2009/0299795, and US2010/0000153. A process plant dimensioned to be transportable by road vehicle to a site of use, such as a wellbore penetrating a small natural gas reservoir, may be configured to have length no greater than 17 meters possibly no greater than 13 meters and width no greater than 3 meters. As suggested by the documents above, the length and width may fit within the footprint of a shipping container approximately 8 feet (2.5 meters) wide and commonly up to 40 feet (12.2 meters) long, although container lengths up to 53 feet (16.2 meters) are in use. Such a transportable unit may be configured to have a vertical height during transport of not more than 8, 9.5 or 10.5 feet (2.5, 2.9 or 3.2 meters) and may be constructed with a total weight not exceeding 30,000 kg and possibly not exceeding 20,000 kg.

Figure 14:
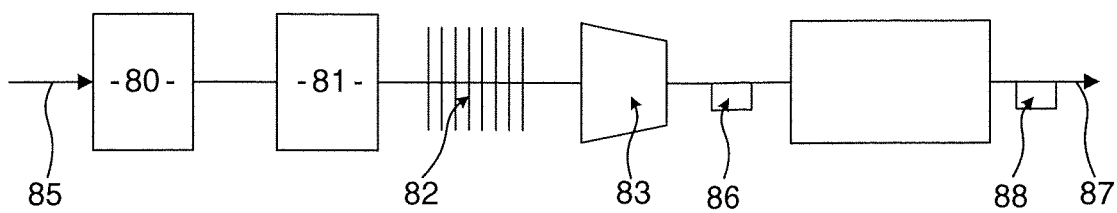
FIG. 14 is a block diagram of a small-scale gas-to-liquid unit producing alkanes.

FIG. 14 is a block diagram which illustrates use of a hydrogen sensor, of the type shown in FIGS. 1 to 3, in a small-scale gas-to-liquid unit converting natural gas to a mixture of alkanes. The sensor is used to determine the concentration of hydrogen gas being generated by a reformer and entering a Fischer-Tropsch reactor. The principal features of this gas-to-liquid unit are a gas pretreatment unit 80, a syngas generator 81, a heat exchanger 82 to lower the temperature of the syngas, a compressor 83 to raise the pressure of the syngas and a Fischer-Tropsch reactor 84. Natural gas enters at 85 and the products exit the Fischer-Tropsch reactor at 87. Other details of the unit are omitted for clarity. The reactor 84 is designed for low temperature Fischer-Tropsch synthesis using a cobalt metal catalyst. Further design parameters are that the inlet temperature and pressure of the syngas are maintained at values of 210° C. and 28.9 bar, respectively.

A hydrogen sensor 86 is located on the syngas flow line immediately before it enters the Fischer-Tropsch reactor 84, i.e., after the syngas has been cooled and compressed. The sensor 86 has the construction shown by FIGS. 1 to 3 except for a different protective layer 25 over the palladium membrane 24. The palladium membrane 24 is highly selective to the transport of hydrogen but its surface may become poisoned by the high concentration of CO in the syngas. The palladium membrane can be protected from contamination by carbon monoxide and other components in the syngas, such as residual water vapour, by the use of a protective layer 25 of silica, possibly 10-100 nm in thickness, deposited on the palladium using chemical vapour deposition. For example, Lee et al., Journal of Membrane Science, 2004, vol. 213, pp. 117-126 have demonstrated that thin films of silica (20-30 nm) deposited on alumina can exhibit a highly selective permeance to hydrogen relative to other gases such as CO and $CO_2$ at temperatures up to 600° C. Alternatively, a thin barrier coating of silicon carbide can be applied to the palladium membrane using a plasma-enhanced chemical vapour deposition technique, as for example described by Zambov et al, Journal of Vacuum Science & Technology A, 2006, vol. 24, pp. 1706-1713.

The ionic liquid used in the sensor 86 is 1-hexyl-3-methylimidazolium bis(trifluoromethylsulfonyl)imide ([hmim][$NTf_2$]) and the working and counter electrodes are composed of platinum, while the pseudo reference electrode is composed of silver. The hydrogen sensor is small, which enables equilibrium between hydrogen in the syngas stream and hydrogen dissolved in the ionic liquid to be established quickly for the determination of the hydrogen concentration. Under the operating conditions the electrochemical measurement determined the dissolved hydrogen concentration to be 0.0453 moles of hydrogen per kilogram of ionic liquid, which equated to 90.6 ppm. The dissolved hydrogen concentration is obtained with a partial pressure of hydrogen in the gas stream of 19.5 bar, which gives a hydrogen/carbon monoxide ratio of 2.07, assuming that syngas behaves as an ideal gas under the operating temperature and pressure conditions.

The concentration of carbon monoxide in the syngas stream can, if desired, be independently monitored using a small infrared gas sensor similar to those described in U.S. Pat. No. 6,995,360, but operating over the wavelength range 4.44-5.00 μm. A second electrochemical hydrogen sensor 88 and a second optical carbon monoxide sensor may if desired be fitted to the flowline 87 downstream of the Fischer-Tropsch reactor 84 to determine the concentrations of unreacted hydrogen and carbon monoxide and hence monitor the efficiency of the process.

Figure 15:
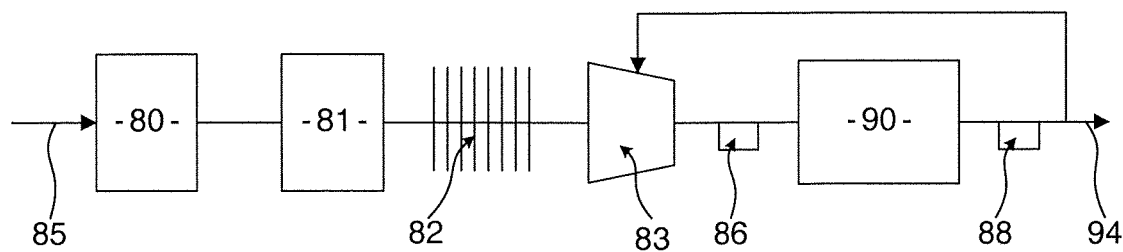
FIG. 15 is a block diagram of a small-scale gas-to-liquid unit producing methanol.

(b) Monitoring the Concentration of Hydrogen in a Portable Methanol Synthesis Reactor FIG. 15 is a block diagram of a small-scale process plant for conversion of natural gas, via syngas to methanol. Parts of the plant correspond to those in FIG. 14 and are shown with the same reference numerals. A reactor 90 converts the syngas to methanol which flows out at 94 This conversion differs from the Fischer-Tropsch process of FIG. 14 in several respects: (i) methanol synthesis is normally carried out at higher total pressures than Fischer-Tropsch synthesis, commonly in the pressure range 50-100 bar; (ii) the conversion of syngas to methanol is low, such as less than 15% conversion in a single reactor stage and therefore after the gas stream leaves leaving the reactor 90 the methanol product is condensed by cooling and separated to flow out at 94 while the unreacted gas mixture, which contains hydrogen, carbon monoxide and carbon dioxide is recycled along line 92 to pass through the reactor again (an alternative is to use a sequence of reactors); (iii) any $CO_2$ present in the gas stream either as a result of its introduction into the syngas or its occurrence in the original natural gas, is converted into methanol.

Hydrogen sensors 86, 88 are used to monitor hydrogen concentrations at the inlet and outlet to reactor 90. The hydrogen sensors may if desired be accompanied by high temperature/high pressure CO and $CO_2$ sensors, as for example described in U.S. Pat. No. 6,995,360. The $CO_2$ is detected in the spectral range 4.17-4.35 μm while CO is detected in the spectral range 4.55-4.76 μm.

The ionic liquid used in the sensors 86, 88 is 1-hexyl-3-methylimidazolium bis(trifluoromethylsulfonyl)imide and the electrode materials are platinum for the working and counter electrodes and silver for the reference electrode. The hydrogen-permeable window separating the ionic liquid from the gas streams has a thin palladium membrane on a porous ceramic support. The membrane can be coated with a suitable barrier material, such as silica or silicon carbide, to protect the palladium membrane from gases such as CO and $H_2O$.

Design parameters for the methanol synthesis reactor shown in FIG. 15 are an inlet temperature of 225° C., an inlet pressure of 55 bar and an internal operating temperature of the reactor of 244° C. The hydrogen/carbon ratio (H/C) in the syngas stream is commonly represented by the ratio $H_2/(2CO+3CO_2)$, which should be in the range 1.00-1.05 for efficient conversion.

A set of further expected parameters was calculated using literature data. The hydrogen sensor 86 on the inlet flow line of the methanol reactor 90 measures a concentration of 0.093 moles of hydrogen per kilogram of ionic liquid (186 ppm), which corresponds to a partial pressure of hydrogen gas of 38.5 bar at 225° C. The infrared gas detector measures the concentrations of CO and $CO_2$ to be 0.304 and 0.093 moles/liter, respectively, which correspond to partial pressures of 12.6 and 3.9 bar, assuming that the gases behave as pure components. If it is assumed that hydrogen in syngas behaves as a pure component, then its concentration is 0.92 moles/liter and therefore the H/C ratio is 1.04.

The temperature and pressure of the gas exiting the methanol reactor are 244° C. and 45.5 bar, respectively, with 3.4 bar of the decrease in pressure due to frictional losses. The hydrogen sensor in the exit gas stream at 244° C. measures a concentration of 0.080 moles of hydrogen per kilogram of ionic liquid (160 ppm), which corresponds to a partial pressure of hydrogen gas of 31.7 bar. Assuming the hydrogen gas behaves as a pure component, its concentration in the exit gas stream is 0.73 moles/liter. The infrared gas sensor measures exit concentrations of CO and $CO_2$ of 0.266 and 0.055 moles/liter, respectively, which, assuming the gases behave as pure components, correspond to partial pressures of 11.45 and 2.35 bar. The known temperature and pressure changes associated with the methanol reactor allow the outlet concentrations of hydrogen, CO and $CO_2$ to be calculated at inlet conditions. Under these conditions, the changes in the concentrations of CO and $CO_2$ are 5.9% and 36.5%, respectively, giving a total carbon conversion of 13.1% of the total inlet carbon concentration. The corresponding decrease in the hydrogen concentration on passing through the methanol reactor is 15.0%.

The gas hourly space velocity (GHSV) in the reactor under standard temperature and pressure conditions is 8000 $hr^{-1}$. Computing from this gives a rate of methanol synthesis of 0.51 kg per liter of catalyst per hour and a rate of water production of 0.19 kg per liter of catalyst per hour at the operating conditions of the reactor.

(c) Monitoring the Hydrogen Consumption in a Portable Hydrocarbon Cracking Reactor The low temperature Fischer-Tropsch synthesis of hydrocarbons gives rise to a wide distribution of chain lengths such that the product contains hydrocarbons which are both liquid and solid hydrocarbons at ambient temperature. The solid hydrocarbon, commonly termed wax, may contain linear hydrocarbons in the range $C_{22}$ to $C_{70}$ and this product frequently accounts for approximately two thirds of the hydrocarbons generated in Fischer-Tropsch synthesis. The wax may be converted to liquid products, such as diesel fuels, by hydrocracking: see for instance Leckel in Energy & Fuels, 2009, vol. 23, pp. 2342-2358.

The cracking reaction results in a decrease in the average hydrocarbon number of the alkane chain and an increase in the average hydrogen:carbon ratio. A measurement of the rate of consumption of hydrogen can therefore be used in predicting the average carbon number of the hydrocarbon product of the cracking reaction.

Figure 16:
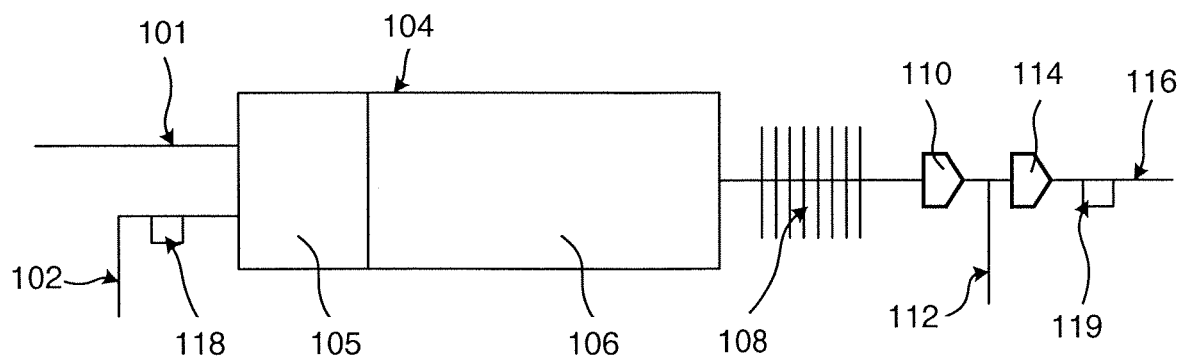
FIG. 16 is a block diagram of a unit for cracking wax produced by a Fischer-Tropsch reactor.

FIG. 16 is a block diagram of process plant used to hydrocrack Fischer-Tropsch wax. Molten wax and hydrogen are supplied along respective lines 101 and 102 to a reactor vessel 104. The molten wax (average hydrocarbon chain length $\bar{n}_i$) and hydrogen gas enter the reactor vessel 104 at mass flow rates of M' and M'$_H$, respectively, where they are mixed in an inert packed bed 105 before being passed into a catalytic bed 106 of platinum metal deposited on an amorphous silica-alumina ($SiO_2$—$Al_2O_3$) substrate. The cracked hydrocarbon (average hydrocarbon chain length $\bar{n}_f$), exits the reactor 104 through a heat exchanger 108. Choke 110 is used to control the pressure drop across the catalytic reactor. The cracked hydrocarbon flowing from choke 110 contains liquid hydrocarbon with hydrocarbon gases and unreacted hydrogen. Liquid product is separated from gas and is removed along outlet line 112 while the gases flow along line 116. The pressure at which the liquid and gas are separated is controlled by choke 110 and the pressure at which the gas passes into line 116 is controlled by a further choke 114. The uncondensed hydrocarbons and unreacted hydrogen from this process may be used as fuel for the burner of the steam reformer 84 in FIG. 14 that generates the syngas for the Fischer-Tropsch synthesis.

Hydrogen sensors 118, 119 of the type shown in FIGS. 1 to 3 are fitted to the hydrogen inlet line 102 and the outlet gas line 116.

Design parameters for the hydrocracking reactor are: mass flow rate of wax M'=266 kg/hour, average initial wax hydrocarbon number $\bar{n}_i$=18.02, inlet hydrogen gas pressure=32 bar, reactor inlet temperature=96° C., inlet mass flow rate of hydrogen M'$_H$=2.66 kg/hour, operating temperature of hydrocracking reactor=340° C., weight hourly space velocity (WHSV)=2.6 kg wax per hour per kg of catalyst, heat exchanger outlet temperature=68° C., and outlet gas line pressure=3 bar A low hydrogen/wax mass flow ratio (M'$_H$/M'=0.01) is used to minimize the use of hydrogen since the unreacted hydrogen is not separated from the produced hydrocarbon vapour for recycling into the hydrocracking reactor. The hydrogen gas sensors 118, 119 are used to measure the concentration of hydrogen in the gas streams in the inlet and outlet lines of the hydrocracking reactor. The ionic liquid used in the gas sensor is 1-hexyl-3-methylimidazolium bis(trifluoromethylsulfonyl)imide ([hmim][NTf$_2$]) and the working and counter electrodes are composed of platinum while the reference electrode is composed of silver. The electrochemical cell of the sensor contacts the hydrogen in the analyte by means of a palladium membrane that is coated with a suitable material, such as silica, to minimize contamination by gases such as carbon monoxide and hydrogen sulfide.

Using literature data and the above design parameters, further expected values were calculated. The input hydrogen sensor 118 measures a hydrogen concentration of 0.0516 moles of hydrogen per kilogram of ionic liquid (103.2 ppm), which corresponds to an equilibrium partial pressure of hydrogen gas of 31.1 bar. This pressure is close to the input gas pressure of 32 bar. Using a sensor to determine the input hydrogen partial pressure (concentration) facilitates using a hydrogen-containing gas mixture if pure hydrogen is not available or too costly. The output hydrogen gas sensor 119 measures a concentration of 0.0019 moles of hydrogen per kilogram of ionic liquid (3.8 ppm), which corresponds to an equilibrium partial pressure of hydrogen gas of 1.29 bar. The combined partial pressure of the low molecular weight hydrocarbons (primarily propane to octane) is approximately 1.7 bar. Assuming that the hydrogen gas behaves as a pure component, the concentration of hydrogen is 0.0454 moles per liter, which compares to an input gas concentration of 0.998 moles per liter. From the flow rate of gas on the outlet gas line the mass flow rate of hydrogen gas is 1.78 kg/hour and therefore the rate of consumption of hydrogen M'$_{HC}$ is 0.88 kg/hour, which is approximately 33% consumption. The ratio M'$_{HC}$/M' is equal to 0.0033 and using the equation:

$$\frac{\bar{n}_f}{\bar{n}_i} = \frac{M'}{M' + (7\bar{n}_i + 1)M'_{HC}}$$

the ratio $\bar{n}_f/\bar{n}_i$ is calculated to be 0.705 giving $\bar{n}_f$=12.71. The hydrocracking of the Fischer-Tropsch wax therefore reduces its average carbon number from 18.02 to 12.71.

(d) Monitoring In Situ Hydrocarbon Upgrading Processes

Figure 17:
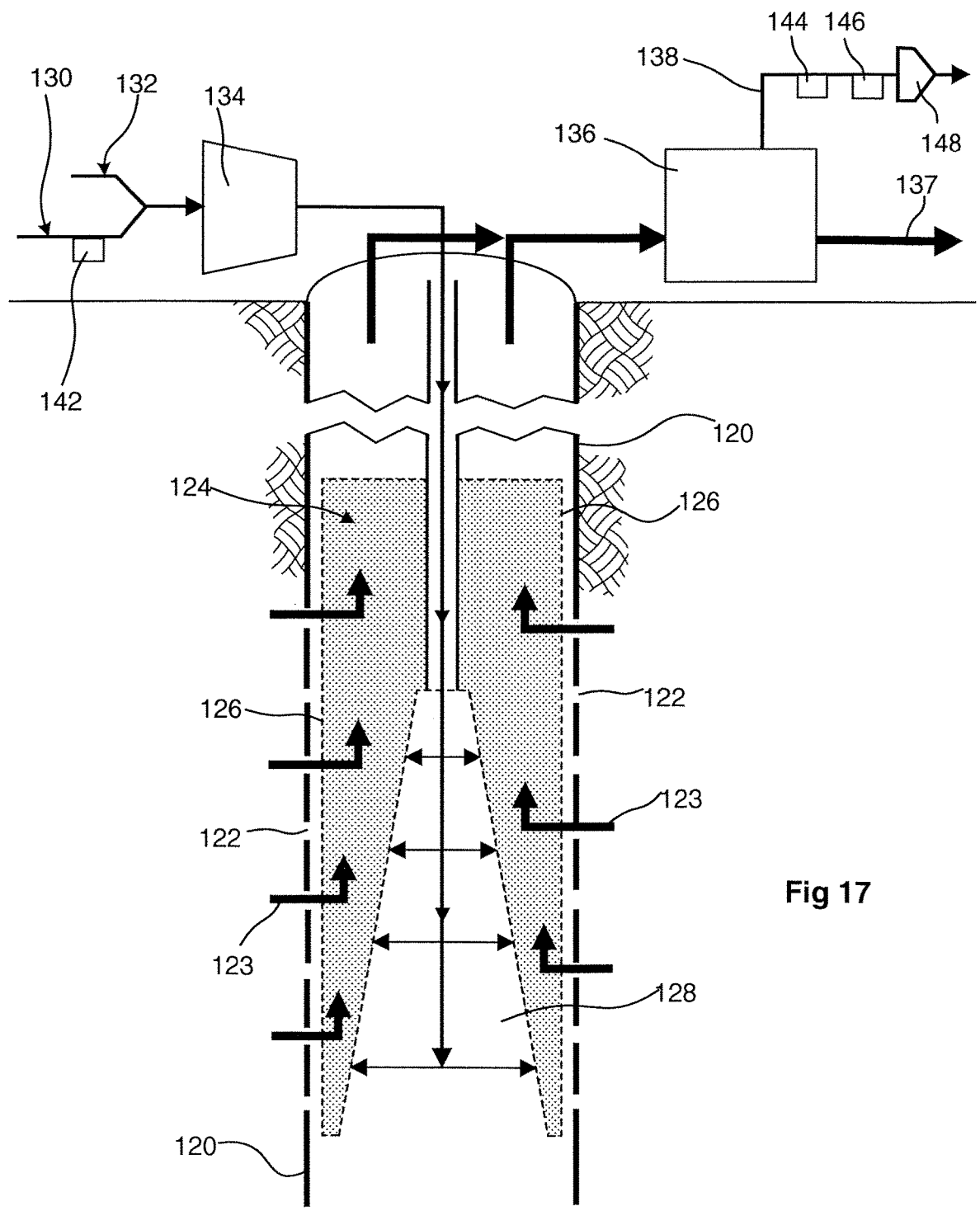
FIG. 17 is a schematic of equipment for modifying heavy oil while it is still below ground.

FIG. 17 shows a schematic of a hypothetical in situ upgrading process for heavy oil being produced from a well. The well has been completed with casing 120, the casing has been perforated as indicated at 122 and the oil-bearing formation around the well has been hydraulically fractured. The resultant fractures are filled with proppant. As indicated by heavy arrows 123, the heavy oil flows through the perforations 122 into a porous bed 124 of catalyst particles downhole within the well. The catalyst bed 124 is enclosed by a metal mesh 126 which is shaped so that the lower part of the bed surrounds a conical cavity 128.

The catalyst bed is heated to a temperature in the range 300-400° C. This may be done with electrical heating powered through cable from the surface or with a liquid, such as silicone oil, that is heated at surface and circulated down to the catalyst bed 124 and back again through pipes in the well. Prior to perforation, the portion of casing which will surround the catalyst bed is provided with a layer of a thermally insulating material on its interior, so that there is thermal insulation between the mesh and the casing. The temperature of the catalyst bed is monitored and maintained by an array of thermocouples used to control the electrical heating or the supply of heated silicone oil.

Natural gas, piped from a natural gas source elsewhere, is consumed in a process for upgrading the heavy oil. Part of this natural gas is burnt to heat silicone oil or generate electricity. The heated oil or electricity is used to heat the catalyst bed. Another part of this natural gas is used as fuel to generate steam. The exhaust gases from burning natural gas are cooled to condense out water, so that the exhaust gas is a mixture of carbon dioxide and nitrogen.

A further part of this natural gas is used as feed for a process plant that generates synthesis gas by reacting the natural gas, which is largely methane, with steam in the presence of a catalyst (e.g., nickel supported on a mixed silica-alumina substrate) at a temperature in the range 850-950° C.:

$$CH_4+H_2O \rightarrow 3H_2+CO$$

The synthesis gas so formed is further reacted with steam in the presence of a second catalyst (e.g., a mixture of iron(III) and chromium(III) oxides) to drive the so-called water gas shift reaction:

$$CO+H_2O \rightarrow CO_2+H_2$$

The resulting hydrogen and carbon dioxide flowing along line 130 are mixed with the nitrogen and carbon dioxide exhaust gases flowing along line 132 and piped to a compressor 134 and thence pumped down to the cavity 128 from which they enter the heated catalyst bed 124. The hydrogen reacts with the heavy oil in the presence of the catalysts in the bed 124 to remove sulfur from the oil and to reduce the molecular weight of the oil's constituent hydrocarbons. The carbon dioxide can dissolve in the heavy oil and reduce its viscosity while the nitrogen aids in lifting the produced hydrocarbon to surface. The catalysts may be molybdenum sulfide for removal of sulfur by hydrodesulfurisation reaction with hydrogen to form hydrogen sulfide together with a solid acid catalyst, such as a mixture of amorphous silica and alumina and a lanthanide metal-exchanged zeolite, for reaction of hydrogen with the heavy oil. When required, the catalyst bed 124 in the containing mesh 126 can be removed to surface for catalyst regeneration or replacement.

The produced oil and gases are separated at surface in a separator 136. The liquid is piped along line 137 and the gases are piped along line 138 which leads to a membrane separation unit (not shown) where unreacted hydrogen is extracted for recycling or combustion. The pressure in the flow line 138 is controlled by a choke 148.

Hydrogen sensors 142, 144 of the type shown in FIGS. 1 to 3 are provided on the hydrogen inlet line 130 and the gas outlet line 138 in order to monitor the efficiency of the upgrading process. Further, a hydrogen sulfide sensor 146 on the outlet gas outlet line 138 can be used to determine the concentration of hydrogen sulfide generated by the hydrodesulfurisation process. The hydrogen sulfide sensor may be as described in U.S. Pat. No. 6,939,717.

Design parameters of the heavy oil production and upgrading process are: pre-compressor gas pressure=2.1 bar, pre-compressor gas temperature=153° C., inlet (post-compressor) gas pressure=158 bar, mean formation depth=1380 m, API gravity of untreated heavy oil=15, density of oil=1.035 tonnes/m³, production rate of oil=700 barrel of oil/day=4800 kg/hour, initial sulfur content of heavy oil=1.70 weight percent, post-separator flow line gas pressure=17.6 bar, and post-separator temperature=102° C.

A number of expected values were computed from the design parameters and literature data. The input hydrogen sensor located before the compressor measures a hydrogen concentration of $3.3 \times 10^{-3}$ moles of hydrogen per kilogram of ionic liquid (0.67 ppm), which corresponds to a partial pressure of 0.168 bar at a temperature of 153° C. The remaining pressure of the gas is due to carbon dioxide and nitrogen from the combustion and the reforming/water gas shift reactions. Assuming the hydrogen in the gas mixture behaves as a pure component, the concentration of hydrogen in the pre-compressed gas is 0.0047 moles per liter of gas. The mass flow rate of hydrogen into the catalytic bed 124 in the well is 96.0 kg per hour.

The output hydrogen sensor 144 located after the oil-gas separator measures a hydrogen concentration of 0.0020 moles of hydrogen per kilogram of ionic liquid (4.0 ppm), which corresponds to a partial pressure of hydrogen of 1.20 bar at a temperature of 102° C. Again, assuming the hydrogen in the gas mixture behaves as a pure component, the concentration of hydrogen in the produced gas beyond the separator is 0.0169 moles per liter of gas. Calculating from the flow rate of gas in the gas line 138 beyond the oil-gas separator, the mass flow rate of hydrogen exiting the well is 80.69 kg per hour and therefore the total consumption of hydrogen in the cracking and hydrodesulfurisation reactor is 15.31 kg per hour.

The hydrogen sulfide sensor measures a hydrogen sulfide concentration of $1.11 \times 10^{-3}$ moles per liter of gas (38 ppm w/v) at a temperature of 102° C. The mass flow rate of hydrogen sulfide from the well is 39.88 kg per hour and therefore the mass flow rate of sulfur released from the heavy oil by hydrodesulfurisation is 37.53 kg per hour. Calculating from the mass flow rate of heavy oil and its sulfur content yield a total mass flow rate of sulfur of 81.60 kg per hour and therefore 46.0% of the sulfur in the heavy oil is removed as hydrogen sulfide. The mass rate of hydrogen consumption of the hydrodesulfurisation process is 2.35 kg per hour and therefore the mass rate of hydrogen consumption by the heavy oil cracking treatment is 12.96 kg per hour. The ratio $M'_{HC}/M'$, as defined in the previous section, is 0.0027.

Detection of a Hydrogen Leak in a Proton Exchange Membrane Fuel Cell

Another application of the hydrogen sensors disclosed here is in the context of fuel cells which generate electricity from an electrochemical reaction of hydrogen and oxygen. A hydrogen sensor may be used to detect hydrogen leakage.

There has been prolonged interest in the use of hydrogen in fuel cells, particularly polymer electrolyte membrane or proton exchange membrane (PEM) fuel cells. The design and operation of PEM fuel cells is well known. A detailed description is provided in Barbir, F., PEM Fuel Cells: Theory and Practice, 2005, Elsevier Academic Press, Amsterdam.

At the fuel cell anode, hydrogen is ionised:

$$H_2 \rightarrow 2H^+ + 2e^-$$

and the protons diffuse through a polymer membrane, commonly an ionomer such as Nafion which is a copolymer of tetrafluoroethylene and sulfonated tetrafluoroethylene, to the cathode where they react with oxygen:

$$2H^+ + 0.5O_2 + 2e^- \rightarrow H_2O$$

The use of hydrogen, even at pressures close to atmospheric, in fuel cells raises potential safety issues from leaks either into the atmosphere or into the cathode region. The latter occurrence may be particularly hazardous since the cathode contains both oxygen and a catalyst, commonly high surface area platinum metal, that may facilitate an explosion.

A significant source of hydrogen leaks in polymer electrolyte membrane (PEM) fuel cells is the polymer membrane itself. The leakage of hydrogen gas through the polymer membrane is termed crossover and as reported by Wu et al. in Journal of Power Sources, 2008, 184, pp. 104-119 can reduce the efficiency of the fuel cell and also degrade the mechanical properties of the membrane. Inaba et al. in Electrochimica Acta, 2006, 51, pp. 5746-5753 have reported that hydrogen crossover can cause excessive heating of the cathode membrane assembly and the membrane and more-over the formation of hydroxyl radicals can cause chemical attack on the membrane and the formation of pinholes. The formation of such pinholes can result in even greater hydrogen crossover with the result that potentially explosive levels of hydrogen can leak into the cathode. Monitoring the cathode region for hydrogen which has leaked into it is made difficult by the presence of larger amounts of oxygen and other materials. A sensor of the kind disclosed here is useful because it provides selective entry of hydrogen into the ionic liquid.

Figure 18:
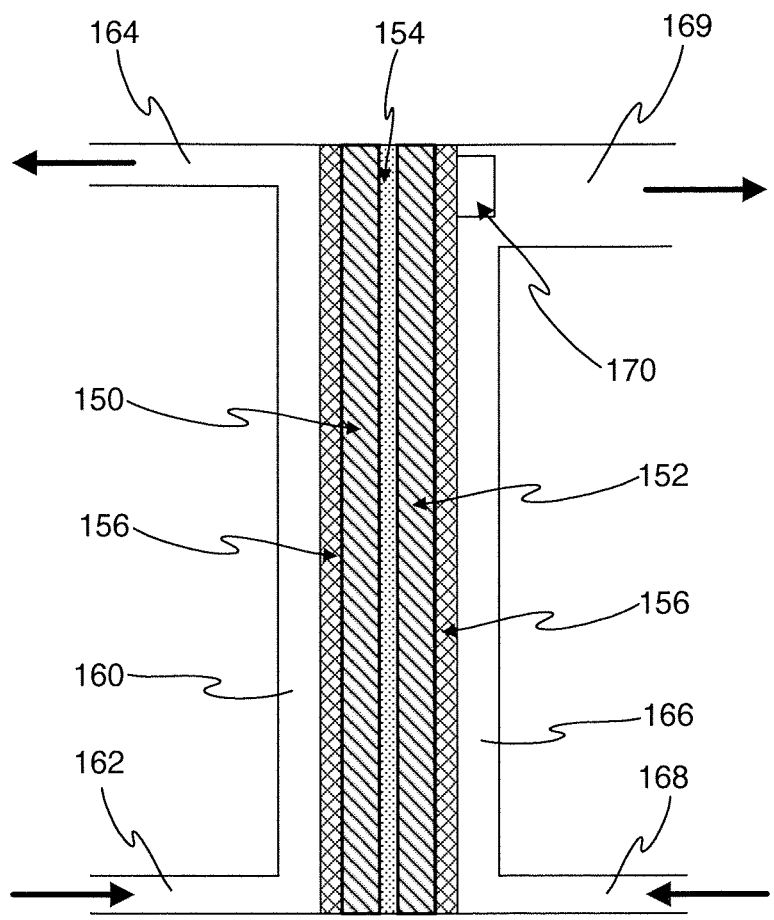
FIG. 18 is a schematic of a PEM fuel cell.

FIG. 18 shows a schematic of a PEM fuel cell. The cell has an anode 150 and cathode 152 separated by a polymer membrane 154. A gas diffusion layer 156 is provided on the surfaces of the anode and cathode exposed to gas in the anode chamber and cathode chamber respectively. A gas diffusion layer is an electrode support layer, which may be composed of carbon to ensure good thermal and electrical conductivity, which gives mechanical support to the membrane and an electrode and enables the hydrogen and oxygen to reach the electrode in a uniform manner. A gas stream containing hydrogen is supplied along input line 162 to the anode chamber 160 and this gas stream with depleted hydrogen content leaves the anode chamber at 164. A gas stream containing oxygen is supplied along line 168 to the cathode chamber 166 and leaves with depleted oxygen content at 169.

A small hydrogen sensor 170 of the type shown in FIGS. 1-3 is located in the cathode chamber 166 of the fuel cell close to the membrane surface and close to the exit 169 of the cathode gas stream in order to detect the rate of hydrogen permeation across the entire membrane. The diameter of the hydrogen sensor may possibly be less than 5 mm. The body of the sensor consists of a material that is electrically insulating, such as ceramic or polymer, and is chemically stable in the presence of oxygen and water vapour at temperatures up to 120° C. The palladium membrane of the sensor 170 is 50 μm in thickness and coated with a thin (200 nm) coating of silica. The ionic liquid used in the electrochemical cell is 1-hexyl-3-methylimidazolium bis(trifluoromethylsulfonyl)imide ([hmim][NTf$_2$]) and the working electrode may be a disk of platinum metal but for greater sensitivity in detecting trace levels of hydrogen palladium nanoparticles can be used as described by Liang et al., "Controllable synthesis of hollow hierarchical palladium nanostructures with enhanced activity for proton/hydrogen sensing", Journal of Physical Chemistry C, 2008, vol. 112, pp. 338-344. The counter electrode is composed of platinum, while the pseudo reference electrode is composed of silver.

The fuel cell is operated under the following conditions: operating temperature=90° C., gas flow rate in anode compartment=1.2 liter/min, relative humidity of gas in anode compartment=100%, total anode gas pressure=3.0 bar, gas flow rate in cathode compartment=1.2 liter/min, relative humidity of gas in cathode compartment=100%, total cathode gas pressure=1.5 bar, area of membrane 154 made of Nafion=100 cm$^2$, and thickness of Nafion membrane 154=50 μm.

The hydrogen sensor measures a concentration of 5.74× 10$^{-6}$ moles of hydrogen per kilogram of ionic liquid (0.015 ppm), which corresponds to an equilibrium partial pressure of 0.0035 bar in the gas stream exiting the cathode. Assuming the oxygen, hydrogen and water vapour in the mixture behave as pure components, the concentration of hydrogen in the exit gas of the cathode is 1.18×10$^{-4}$ moles per liter.

The concentration of hydrogen $C_{H2}$ in the gas exiting the cathode is related to the flux $J_{H2}$ across the hydrogen-permeable membrane of the sensor by $$C_{H2} = \frac{J_{H2}}{Q_C}$$

where $Q_C$ is the total flow rate of gas through the cathode compartment. With $Q_C$=1.2 liter/min the flux $J_{H2}$ is 1.41× 10$^{-4}$ moles per min across the entire membrane, which yields a specific flux of 2.4×10$^{-8}$ moles/cm$^2$/s. The sensor can be used to monitor the hydrogen crossover flux through the membrane and indicate when it is above an acceptable level that is determined by considerations of safety or performance.

In this embodiment a single hydrogen sensor 170 is used, but it will be appreciated that an array of hydrogen sensors distributed throughout the cathode chamber 166 and hence distributed over the area of the cathode 152 could be provided if desired.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

What is claimed is:

1. A process for determining a content of hydrogen in a subterranean fluid medium, the process comprising:
   contacting the subterranean fluid medium with a sensor which comprises a housing enclosing a chamber containing a quantity of electrolyte which is an ionic liquid electrolyte, a window which is permeable to hydrogen positioned in an opening in the housing, a plurality of electrodes in contact with the ionic liquid electrolyte in the chamber, and a sensing unit enclosed within the chamber and configured to monitor at least one of a temperature or a pressure of the subterranean fluid medium;
   allowing hydrogen to pass through the window from the subterranean fluid medium into the electrolyte;
   heating the sensor to a sensor temperature above a prevailing temperature of the subterranean fluid medium where the prevailing temperature is at least 100° C.;
   determining at least one of the temperature or the pressure of the subterranean fluid medium with the sensing unit;
   applying electrical potential to the plurality of electrodes;
   measuring a current flow; and
   determining the content of hydrogen based on the current flow and at least one of the temperature or the pressure of the subterranean fluid medium.

2. The process according to claim 1, further comprising allowing a hydrogen concentration across the window to reach an equilibrium.

3. The process according to claim 2, wherein heating the sensor reduces an amount of time it takes for the hydrogen concentration across the window to reach the equilibrium.

4. The process according to claim 1, wherein the sensor is heated by the subterranean fluid medium.

5. The process according to claim 1, wherein the sensing unit is a combined temperature and pressure sensor.

6. The process according to claim 1, further comprising maintaining the sensor temperature at a fixed temperature.

7. The process according to claim 1, wherein the window comprises a hydrogen permeable metal membrane that is selectively permeable to hydrogen.

8. The process according to claim 1, wherein the window comprises a hydrogen permeable membrane on a porous support, the membrane comprising a sheet of metal that is selectively permeable to hydrogen.

9. The process according to claim 8, wherein the sheet of metal that is selectively permeable to hydrogen is not more than 200 μm thick.

10. The process according to claim 8, wherein the sheet of metal that is selectively permeable to hydrogen is overlaid with a protective layer.

11. The process according to claim 1, wherein the window comprises a hydrogen permeable membrane on a porous support, the membrane comprising a polymer film and a layer of metal that is selectively permeable to hydrogen deposited on the polymer film.

12. The process according to claim 1, wherein the ionic liquid electrolyte fills the chamber and a concentration of water in the ionic liquid electrolyte is not more than 1% by weight.

13. The process according to claim 1, wherein an electrode of the plurality of electrodes comprises palladium nanoparticles.

14. The process according to claim 1, wherein the sensor is part of a downhole tool.

15. The process according to claim 1, wherein the sensor is connected to a protective enclosure containing a fiber-optic cable.

16. The process according to claim 1, wherein the subterranean fluid medium is a flow stream which is a feedstock, product, intermediate product or exhaust of at least one chemical reaction which consumes or generates hydrogen.

17. The process according to claim 16, wherein the at least one chemical reaction is any one of:
   partial oxidation of methane to syngas;
   Fischer-Tropsch conversion of syngas to alkanes and water;
   methanol synthesis;
   hydrocracking of hydrocarbons;
   water gas shift reaction; or
   hydrodesulfurization.

18. The process according to claim 1, wherein the process is carried out in a well that is equipped for carrying out upgrading of hydrocarbon by reaction with hydrogen at a downhole location, and wherein the subterranean fluid medium is a flow stream which is a feedstock to the well or produced therefrom.

19. The process according to claim 1, wherein the process is carried out with the sensor located in a fuel cell at a position to detect a leakage of hydrogen in the fuel cell.

20. The process according to claim 19, wherein the fuel cell is a polymer electrolyte membrane fuel cell that comprises a cathode exposed to a cathode gas stream containing hydrogen and an anode exposed to an anode gas stream containing oxygen and the sensor is located at a position to detect a leakage of hydrogen from the cathode gas stream into the anode gas stream.

* * * * *